United States Patent
Calabro et al.

(10) Patent No.: US 7,368,502 B2
(45) Date of Patent: May 6, 2008

(54) HYDROXYPHENYL CROSS-LINKED MACROMOLECULAR NETWORK AND APPLICATIONS THEREOF

(75) Inventors: Anthony Calabro, Cleveland Heights, OH (US); Richard A. Gross, Plainview, NY (US); Aniq B. Darr, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 441 days.

(21) Appl. No.: 11/198,803

(22) Filed: Aug. 5, 2005

(65) Prior Publication Data

US 2005/0265959 A1  Dec. 1, 2005

Related U.S. Application Data

(62) Division of application No. 10/753,779, filed on Jan. 8, 2004, now Pat. No. 6,982,298.

(51) Int. Cl.
*C08L 89/00* (2006.01)
*C08G 63/48* (2006.01)

(52) U.S. Cl. ............... 525/54.1; 525/54.2; 525/326.1; 525/420; 525/540; 527/600; 521/189; 521/180

(58) Field of Classification Search ............... 525/54.1, 525/54.2, 326.1, 420, 540; 521/180, 189; 527/600
See application file for complete search history.

(56) References Cited

U.S. PATENT DOCUMENTS

| 4,277,582 A | 7/1981 | Mueller et al. |
| 4,350,629 A | 9/1982 | Yannas et al. |

(Continued)

FOREIGN PATENT DOCUMENTS

EP  0 516026 A1  12/1992

(Continued)

OTHER PUBLICATIONS

Blumenkrantz, N. and Asboe-Hansen, G. (1973) New method for quantitative determination of uronic acids. Anal. Biochem. 54, 484-489.

(Continued)

*Primary Examiner*—Irina S Zemel
(74) *Attorney, Agent, or Firm*—Pearne & Gordon LLP

(57) ABSTRACT

A dihydroxyphenyl cross-linked macromolecular network is provided that is useful in artificial tissue and tissue engineering applications, such as artificial or synthetic cartilage. The network is made by first providing a polyamine or polycarboxylate macromolecule (having a plurality of amine or carboxylic acid groups respectively attached along the length of the molecule), reacting this macromolecule with a hydroxyphenyl compound having a free carboxylic acid group in the case of a polyamine or a free primary amine group in the case of a polycarboxylate, and substituting the hydroxyphenyl compound onto the macromolecule via a carbodiimide-mediated reaction pathway to provide a hydroxyphenyl-substituted macromolecule. This macromolecule is then linked to other such macromolecules via an enzyme catalyzed dimerization reaction between two hydroxyphenyl groups attached respectively to different macromolecules under metabolic conditions of temperature and pH. In a preferred embodiment, the macromolecular network is made up of tyramine-substituted hyaluronan molecules that are linked by dityramine bonds to provide a stable, coherent hydrogel with desired physical properties. A method of preparing such a network is also provided.

27 Claims, 4 Drawing Sheets

U.S. PATENT DOCUMENTS

| | | | |
|---|---|---|---|
| 5,017,229 | A | 5/1991 | Burns et al. |
| 5,769,899 | A | 6/1998 | Schwartz et al. |
| 6,251,876 | B1 | 6/2001 | Bellini et al. |
| 6,586,493 | B1 | 7/2003 | Massia et al. |
| 2001/0027237 | A1 | 10/2001 | Mayes et al. |
| 2004/0063206 | A1 | 4/2004 | Rowley et al. |
| 2004/0127698 | A1 | 7/2004 | Tsai et al. |

FOREIGN PATENT DOCUMENTS

| | | |
|---|---|---|
| EP | 0 718312 A2 | 6/1996 |
| EP | 1312383 A2 | 5/2003 |
| JP | 54-36388 | 3/1979 |
| JP | 7-102002 | 4/1995 |
| JP | 8085703 | 4/1996 |
| JP | 2002-080501 | 3/2002 |
| JP | 2003-010308 | 1/2003 |
| WO | 85/04413 | 10/1985 |
| WO | 89/02445 | 3/1989 |
| WO | 89/07426 | 8/1989 |
| WO | 90/09769 | 9/1990 |
| WO | 93/07862 | 4/1993 |
| WO | 97/18244 | 5/1997 |
| WO | 99/57301 | 11/1999 |
| WO | 00/01733 | 1/2000 |
| WO | 00/16818 | 3/2000 |
| WO | 00/46252 | 8/2000 |
| WO | 00/54762 | 9/2000 |
| WO | 01/00792 | 1/2001 |
| WO | 01/85845 | 11/2001 |
| WO | 02/18450 | 3/2002 |
| WO | 02/060375 | 8/2002 |
| WO | 02/068383 | 9/2002 |
| WO | 03/006068 | 1/2003 |
| WO | 03/007879 | 1/2003 |
| WO | 03/018033 | 3/2003 |
| WO | 03/018044 | 3/2003 |
| WO | 03/061626 | 7/2003 |
| WO | 03/072157 | 9/2003 |
| WO | 03/076475 | 9/2003 |
| WO | 04/050712 | 6/2004 |

OTHER PUBLICATIONS

Calabro, A., Benavides, M., Tammi, M., Hascall, V.C. and Midura, R.J. (2000) Microanalysis of enzyme digests of hyaluronan and chondroitin/dermatan sulfate by fluorophore-assisted carbohydrate electrophoresis (FACE). Glycobiology, 10, 273-281.

Calabro, A., Hascall, V.C. and Midura, R.J. (2000) Adaptation of FACE methodology for microanalysis of total hyaluronan and chondroitin sulfate composition from cartilage. Glycobiology, 10, 283-293.

Mow, V.C., Kuei, S.C., Lai, W.M., and Armstrong, C.G. (1980) Biphasic creep and stress relaxation of articular cartilage in compression: theory and experiments. J. Biomech. Engin. 102, 73-84.

Jurvelin, J.S., Buschmann, M.D., and Hunziker, E.B. (1997) Optical and mechanical determination of Poisson's ratio of adult bovine humeral articular cartilage. J. Biomech. 30(3), 235-241.

Soltz, M.A., Ateshian, G.A. (2000) A conewise linear elasticity mixture model for the analysis of tension-compression nonlinearity in articular cartilage. J. Biomech. Engin. 122, 576-586.

Sehgal, D. and Vijay, I.K. (1994) A method for the high efficiency of water-soluble carbodiimide-mediated amidation. Anal Biochem. 218, 87-91.

Kalra, B., Kumar, A. and Gross, R.A. (2000) Gel formation by enzyme-selective crosslinking of tyramine decorated poly(aspartamide). Polymer Preprints 2000, 41(2), 1804-1805.

de la Motte, C.A., Hascall, V.C., Calabro, A., Yen-Lieberman, B. and Strong, S.A. (1999) Mononuclear leukocytes preferentially bind via CD44 to hyaluronan on human intestinal mucosal smooth muscle cells after virus infection or treatment with poly(I:C). J. Biol. Chem. 274, 30747-30755.

Buckwalter, J.A. and Mankin, H.J. (1997) Articular cartilage: Degeneration and osteoarthrosis, repair, regeneration, and transplantation. J. Bone Joint Surg. [Am] 79A, 612-632.

Brittberg, M., Lindahl, A., Nilsson, A., Ohlsson, C., Isaksson O. and Peterson L. (1994) Treatment of deep cartilage defects in the knee with autologous chondrocyte transplantation. N. Engl. J. Med. 331, 889-895.

Hunziker, E.B. and Rosenberg, L.C. (1996) Repair of partial-thickness defects in articular cartilage: Cell recruitment from the synovial membrane. J. Bone Joint Surgery [Am] 78A, 721-733.

Pouyani, T., Kuo, J.W., Harbison, G.S. and Prestwich, G.D. (1992) Solid-state NMR of N-acylureas derived from the reaction of hyaluronic acid with isotopically-labeled carbodiimides, J. Am. Chem. Soc. 114, 5972-5976.

Bulpitt, P. and Aeschlimann, D. (1999) New strategy for chemical modification of hyaluronic acid: Preparation of functionalized derivatives and their use in the formation of novel biocompatible hydrogels. J. Biomed. Mater. Res. 47, 152-169.

Gross, A.J. (1954) The oxidation of tyramine and related compounds by peroxidase. Ph.D. Thesis, MIT, pp. 1-84.

Aslam, M. and Dent, A. (1998) Bioconjugation: Protein Coupling Techniques for the Biomedical Sciences. Chapter 5, pp. 216-363. Macmillan Reference Ltd., London, UK.

Aslam, M. and Dent, A. (1998) Bioconjugation: Protein Coupling Techniques for the Biomedical Sciences. Chapter 6, pp. 364-482. Macmillan Reference Ltd., London, UK.

Arthur J. Gross and Irwin W. Sizer, "The Oxidation of Tyramine, Tyrosine, and Related Compounds by Peroxidase," Dept. of Biology, MIT, vol. 234, No. 6, pp. 1611-1614, 1959.

Mary C. Wells-Knecht, et al., "Oxidized Amino Acids in Lens Protein with Age," The Journal of Biological Chemistry, vol. 268, No. 17, pp. 12348-12352, 1993.

Svend Olav Andersen, "Regional differences in degree of resilin cross-linking in the desert locust, Schistocerca gregaria," Insect Biochemistry and Molecular Biology 34, pp. 459-466, 2004.

Andersen, Svend Olav: "Cross-links in resilin identified as dityrosine and trityrosine", Biochimica Et Biophysica Acta, General Subjects, vol. 93, No. 1, 1964, pp. 213-215, XP002363818, Copenhagen.

Thornton, Thomas D.; Savage, Phillip E.: "Phenol oxidation pathways in supercritical water", Industrial & Engineering Chemistry Research, vol. 31, 1992, pp. 2451-2456, XP002363819.

HYDROXYPHENYL CROSS-LINKED MACROMOLECULAR NETWORK AND APPLICATIONS THEREOF

This application is a divisional application of U.S. patent application Ser. No. 10/753,779, filed Jan. 8, 2004 now U.S. Pat. No. 6,982,298.

BACKGROUND OF THE INVENTION

Articular cartilage performs an essential function in healthy joints. It is responsible for absorbing and dissipating impact and frictional loads in order to divert these loads away from bones, to protect the bones from damage. Cartilage performs this function by transferring the loading force to a fluid phase within a three-dimensional network of aggrecan molecules, themselves constrained (described in the next paragraph) within the joint space. Aggrecan molecules have up to 100 chondroitin sulfate chains attached to a core protein, with each chondroitin sulfate chain possessing multiple negatively charged sulfate groups along their length. The effect of all these sulfate groups is to cause each of the chondroitin sulfate chains in a single aggrecan molecule to repel one another, (resulting in the aggrecan molecule having the maximum possible volume at rest), and also to cause adjacent aggrecan molecules in a cartilage aggregate to repel one another.

In healthy cartilage, aggrecan molecules are attached to long hyaluronan chains, which are in turn constrained in large cartilage aggregates within the joint space by an extracellular collagen fibril matrix. Thus, even though adjacent chondroitin sulfate chains in each aggrecan molecule (and adjacent aggrecan molecules attached to the same or a different hyaluronan chain) repel one another, they are nonetheless constrained within the collagen matrix. See FIG. 1 depicting normal, healthy cartilage. Because the chondroitin sulfate chains are so repulsive, the hyaluronan-aggrecan network (or macromolecular network) expands as much as possible within the constraints of the collagen matrix to achieve the lowest possible energy state at rest; i.e. to allow the maximum possible spacing between adjacent negatively charged sulfate groups. As a result, network molecules are highly resistant to being shifted or displaced in order to avoid approaching an adjacent network molecule. These large cartilage aggregates are trapped at one fifth their free solution volume within a meshwork of collagen fibers, which resist any further swelling. Cartilage aggregates with their high negative charge density bind large solvent domains, and contribute to cartilage's ability to absorb loads and resist deformation. Upon compression, the distance between the fixed-negative charge groups on the proteoglycans decreases, which increases the charge-to-charge repulsive forces as well as the concentration of free-floating positive. counterions (such as $Ca^{2+}$ and $Na^+$). Both effects contribute to the viscoelastic nature of cartilage and its ability to resist deformation and absorb compressive loads, further described below.

Within the macromolecular network are water molecules which provide a substantially continuous fluid phase. The macromolecular network diverts impact and frictional loads away from bones by transferring them to the continuous fluid (water) phase as follows. As a joint undergoes a load, the force is absorbed first by the macromolecular network, where it acts on and tends to deform or compress the network. The force sets up pressure gradients in the fluid phase in order to induce fluid flow to accommodate network deformation or compression resulting from the load. But the fluid cannot negotiate the tight macromolecular network, packed with the repulsive chondroitin sulfate chains, sufficiently to accommodate a bulk flow of water without shifting or displacing the network molecules. Hence, individual water molecules may diffuse within the network, but the bulk fluid phase is substantially constrained from flowing through the network except at a much slowed rate due to the resistance to displacement of network molecules. Because the water molecules cannot flow readily despite the pressure gradients, the energy from the impact or frictional load is transferred to and absorbed by the fluid phase where it contributes to compressing the liquid water until the water can be sufficiently displaced to accommodate the network conformation and the pressure gradients have subsided. The overall result is that cartilage absorbs the potentially harmful load, thereby diverting it from bone.

Through this elegant mechanism, normal cartilage is capable of absorbing significant loads by transferring the bulk of the loading force to a fluid phase constrained within a macromolecular network. This arrangement has yet to be adequately duplicated via artificial or synthetic means in the prior art. Consequently, there is no adequate remedy for cartilage degenerative disorders, such as arthritic disorders, where the aggrecan molecules become separated from their hyaluronan chains and are digested or otherwise carried out from the cartilage aggregates.

Osteoarthritis and rheumatoid arthritis affect an estimated 20.7 and 2.1 million Americans, respectively. Osteoarthritis alone is responsible for roughly 7 million physician visits a year. For severe disabling arthritis, current treatment involves total joint replacement with on average 168,000 total hip replacements and 267,000 total knee replacements performed per year in the U.S. alone. Defects in articular cartilage present a complicated treatment problem because of the limited capacity of chondrocytes to repair cartilage. Treatment strategies to date have focused on the use of autologous chondrocytes expanded in culture or the recruitment of mesenchymal stem cells in vivo by chemotactic or mitogenic agents. The intent of these strategies is to increase and/or activate the chondrocyte population so as to resynthesize a normal, healthy articular cartilage surface. One major difficulty associated with these strategies is the inability to maintain these agents at the site of the defect. Hyaluronan has been proposed as a candidate for the development of biomaterials for local delivery of chondrocytes or bioactive agents because of its unique properties, including excellent biocompatibility, degradability, and rheological and physiochemical properties. However, it has been unknown whether chondrocytes suspended in a tissue engineered hyaluronan matrix would be able to synthesize a new cartilage matrix with mechanical properties comparable to normal, healthy articular cartilage. This is because conventional biomaterials made from hyaluronan are formed through chemistries that are incompatible with maintaining cell viability. Chondrocytes must be introduced to the matrices after matrix formation with variable and normally poor results.

Accordingly, there is a need in the art for an artificial or synthetic matrix that can effectively divert a loading force from bones in an effective manner. Preferably, such a matrix can be provided in situ or in vivo to repair or replace articular cartilage during an orthopedic surgical procedure. Most preferably, the artificial or synthetic matrix can be provided to an in situ or in vivo target site as a liquid or a plurality of liquids, and can set up in place to provide a substantially seamless integration with existing cartilaginous and/or bony tissue in a patient.

SUMMARY OF THE INVENTION

A macromolecular network is provided including the following structure

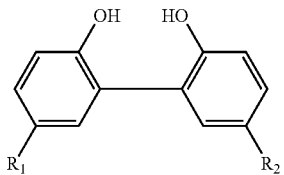

wherein $R_1$ and $R_2$ each is or includes a structure selected from the group consisting of polycarboxylates, polyamines, polyhydroxyphenyl molecules, and copolymers thereof, and wherein $R_1$ and $R_2$ can be the same or different structures.

A macromolecular network is also provided having a plurality of tyramine-substituted hyaluronan molecules, wherein at least two adjacent hyaluronan molecules are linked by a dityramine linkage.

A hydrogel is also provided which includes a macromolecular network of tyramine-substituted hyaluronan molecules that are cross-linked by dityramine linkages between hyaluronan molecules.

A method of making a macromolecular network is also provided including the steps of providing a first macromolecular species selected from the group consisting of hydroxyphenyl-substituted polycarboxylates, hydroxyphenyl-substituted polyamines, other polyhydroxyphenyl molecules, and copolymers thereof, and forming at least one dihydroxyphenyl linkage between two hydroxyphenyl groups attached respectively to adjacent ones of the first macromolecular species.

A method of making a hydrogel is also provided having the following steps:
a) providing a first solution having either a peroxidase enzyme or a peroxide but not both, and also a macromolecular species selected from the group consisting of hydroxyphenyl-substituted polycarboxylates, hydroxyphenyl-substituted polyamines, other polyhydroxyphenyl molecules, and copolymers thereof; b) providing a second solution having the one of the peroxidase enzyme or peroxide not provided in the first solution; and
c) combining the first and second solutions to initiate dihydroxyphenyl cross-linking to form the hydrogel.

DETAILED DESCRIPTION OF PREFERRED EMBODIMENTS OF THE INVENTION

As used herein, the term polycarboxylate means a molecule, structure or species having a chain length of at least two functional groups or units, wherein at least two such groups or units of the chain are or comprise carboxylic acid groups that are sterically accessible to a nucleophilic substitution reaction as described herein. Also as used herein, the term polyamine means a molecule, structure or species having a chain length of at least two functional groups or units, wherein at least two such groups or units of the chain are or comprise primary amine groups that are available for a nucleophilic substitution reaction. Also as used herein, a polyhydroxyphenyl molecule means a molecule having a chain length of at least two functional groups or units, wherein at least two such groups or units of the chain are or comprise hydroxyphenyl groups that can be linked to another hydroxyphenyl group via a C—C bond. Also as used herein, a hydrogel is a material that is prepared comprising a macromolecular network that is used or useful in tissue replacement or engineering applications, e.g. as artificial cartilage, as a material to coat surgical instruments to prevent tissue irritation, or to provide a semi-permeable membrane such as for use in an artificial kidney, etc.

The invention includes a novel structure of a macromolecular network that has been formed by linking hydroxyphenyl groups attached to adjacent long chain macromolecules, resulting in effectively cross-linking the macromolecules to provide a large network. The basic cross-linking structure of the network is shown below

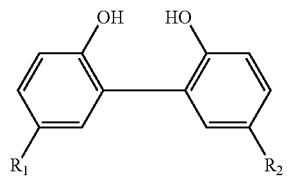

where $R_1$ and $R_2$ are each long chain macromolecules. $R_1$ and $R_2$ can be the same molecule or different molecules, but it will be understood that to provide a suitable network, $R_1$ and $R_2$ will be different molecules for at least a portion of the dihydroxyphenyl linkages in a network according to the invention. It is not necessary, though it is preferred, that $R_1$ and $R_2$ are the same species of molecule.

Figure 1:
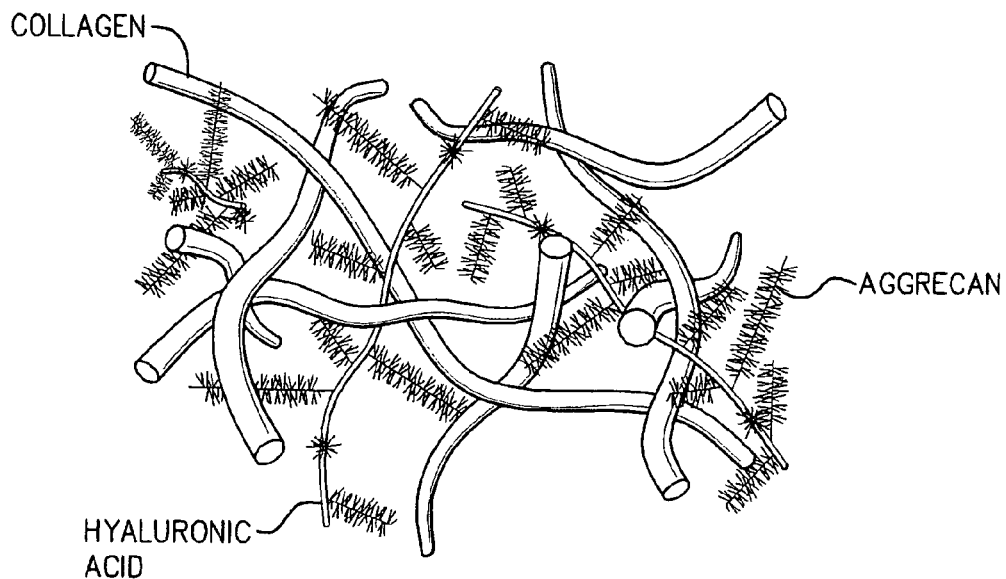
FIG. 1 is a schematic diagram of normal, healthy human cartilage.
Figure 2:
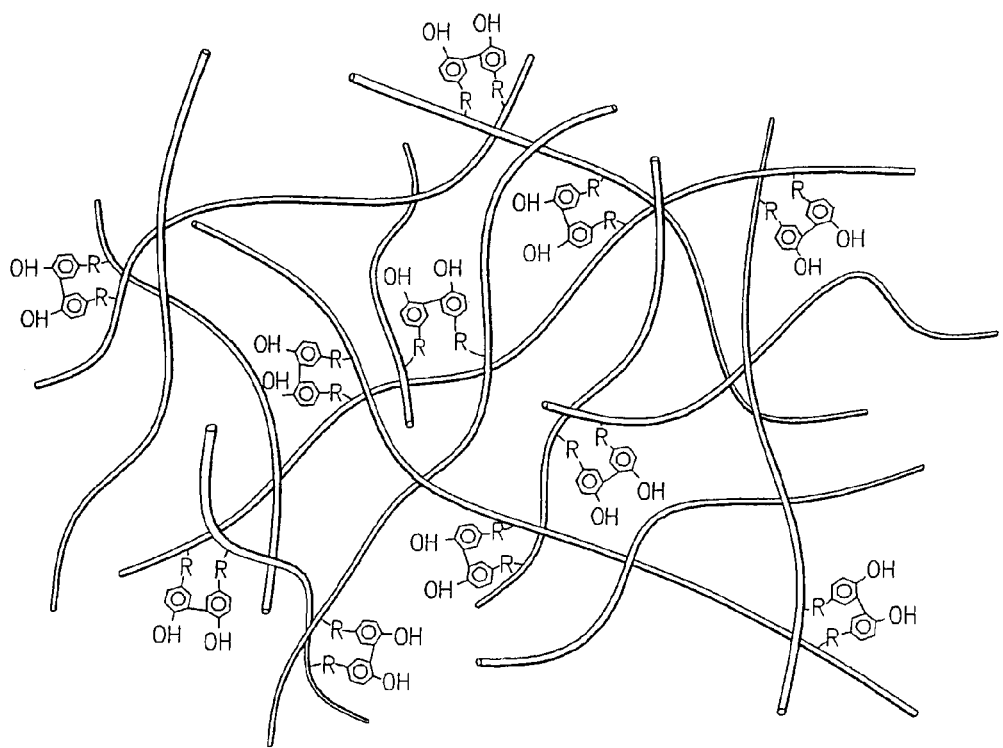
FIG. 2 is a schematic diagram of a dihydroxyphenyl cross-linked macromolecular network according to the invention.

By providing a plurality of these dihydroxyphenyl linkages between adjacent macromolecules, a network of dihydroxyphenyl cross-linked macromolecules is provided as shown schematically in FIG. 2. In the figure, the macromolecules are represented schematically by cylindrical strands, each having at least two hydroxyphenyl groups attached along its length. It is noted that not every hydroxyphenyl group must be linked to another hydroxyphenyl group.

Briefly, the disclosed invention involves covalent coupling of hydroxyphenyl containing compounds, including but not limited to tyramine, through their primary amine (or carboxyl) groups to carboxyl (or primary amine) groups on various polymeric scaffold materials, including but not limited to hyaluronan or chondroitin sulfate (e.g. in the form of aggrecan), via a carbodiimide-mediated reaction. After isolation and purification of the hydroxyphenyl-substituted polymeric scaffolds, the hydroxyphenyl residues are selectively cross-linked by horseradish peroxidase (HRP) in the presence of very dilute hydrogen peroxide to form hydrogels.

The first step in providing the macromolecular network is to prepare or provide the long-chain macromolecules having periodic hydroxyphenyl groups attached. In one embodiment, the macromolecules are polyhydroxyphenyl molecules which already have multiple or periodic hydroxyphenyl groups, such as polyphenols. Suitable polyphenols include polyamino acids (e.g. polytyrosine), epigallocatechin (EGC), and epigallocatechin gallate (EGCG) isolated from green tea, less preferably other polyphenols.

In a further embodiment, the hydroxyphenyl groups can be added to the macromolecules periodically or randomly along their length via a chemical reaction. A preferred method of adding hydroxyphenyl groups to the macromolecules is to utilize a carbodiimide-mediated substitution reaction pathway to provide an amide bond between a primary amine having a hydroxyphenyl group and a carboxylic acid group attached to the macromolecules. In this method, the long-chain macromolecule preferably is a polycarboxylate molecule, having periodic carboxylic acid groups along its length. The hydroxyphenyl groups are provided as part of smaller molecules having primary amine groups that can be attached to the carboxyl carbon atoms of a carboxylic acid group on the long-chain macromolecules via the carbodiimide pathway. The reaction proceeds as follows:

Structure D is a primary amine having a hydroxyphenyl group;

Structure E is a hydroxyphenyl-substituted polycarboxylate; and

Structure F is an acylurea byproduct;

wherein individual Rs can be individually selected, the same or different from one another, to be a straight chain or branched alkane or acyl group, or any other structure that does not interfere with the carbodiimide reaction pathway to provide the amide bond between the $NH_2$ and $CO_2H$ groups as shown in Structure E above.

In the above-illustrated pathway, Reaction A represents a carbodiimide activation of the carboxyl group to provide an activated O-acylisourea intermediate. The electropositive carbon atom of this intermediate is receptive to nucleophilic attack by the lone pair of electrons on a nitrogen atom of an adjacent primary amine molecule having an attached hydroxyphenyl group. The products of this nucleophilic substitution reaction (Reaction B) are a hydroxyphenyl-substituted polycarboxylate and an acylurea byproduct which can be dialyzed out to provide a substantially pure hydroxyphenyl-substitute polycarboxylate product.

Certain side-reactions are possible in the above-described carbodiimide reaction pathway chemistry and should be considered by the person having ordinary skill in the art. First, the carbodiimide can react with nucleophiles other than the carboxylate oxygen atom of the polycarboxylate

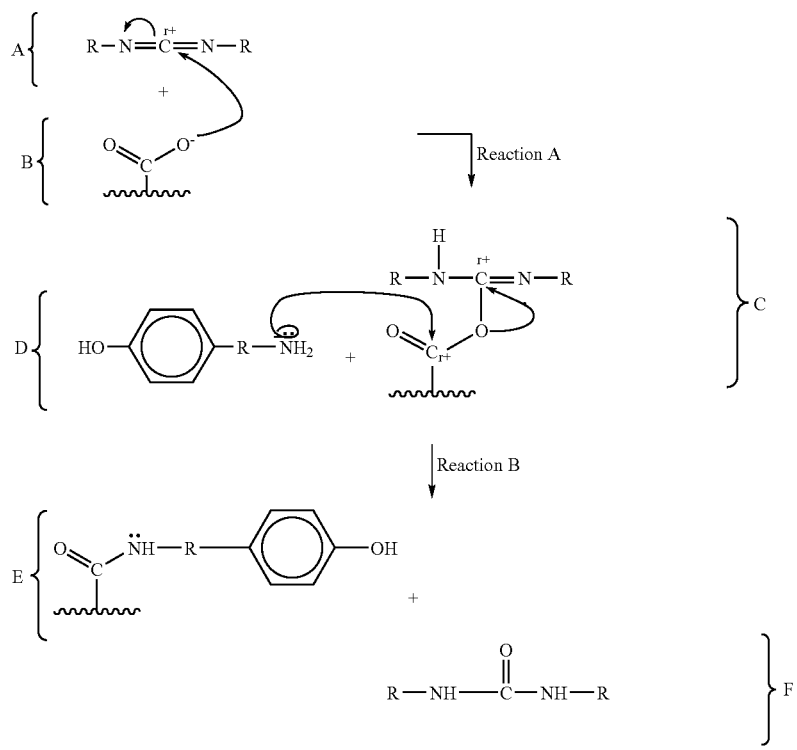

where:
Structure A is a carbodiimide;
Structure B is a polycarboxylate (though only one $CO_2H$ group is shown);
Structure C is the product of Reaction A and is an activated O-acylisourea;

molecule required to form the desired O-acylisourea (reaction A). Such nucleophiles may include the amine and/or hydroxyphenyl groups of Structure D illustrated above. In particular, there are three potential side-reactions for Reaction A which can reduce the effective concentration of the carbodiimide and the primary amine having the hydroxyphenyl group (Structures A and D), and potentially lead to the creation of undesired adducts on the polycarboxylate (Structure B):

Reaction C:

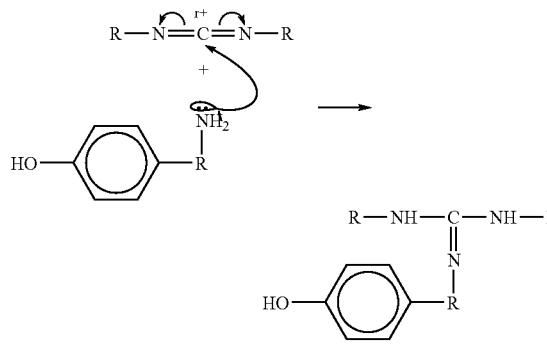

Reaction D:

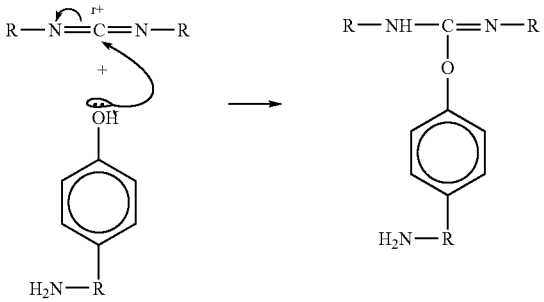

Reaction E:

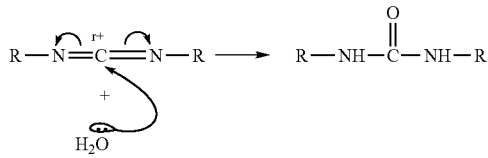

The product of an amine reaction with the carbodiimide (Reaction C) will not have a free amine group effectively reducing the amount of tyramine available for reaction with the O-acylisourea. This reaction also reduces the amount of carbodiimide available for formation of the desired O-acylisourea. The products of the hydroxyphenyl reaction (Reaction D) are not UV absorbent, which will make their detection by UV-spectroscopy in the final hydroxyphenyl-substituted polycarboxylate product (explained below) more difficult. However, because these products still contain free amine groups, they can form amide bonds with the polycarboxylate molecule via Reaction B. This can give rise to two unproductive hyaluronan-substituted structures, neither of which can participate in the peroxidase cross-linking reaction in the second step (described below) of preparing the cross-linked network according to the invention due to the absence of an extractable phenolic hydroxyl hydrogen atom needed to generate the free radical (also explained below). Finally, the carbodiimide can react non-productively with water (Reaction E) to produce the same acylurea shown above as a byproduct of Reaction B, but with none of Structure E, the desired product.

Once the desired O-acylisourea product has been formed in Reaction A, there is again the possibility for certain additional side-reactions:

Reaction F:

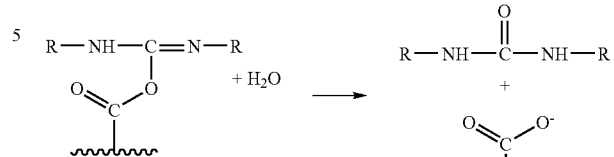

Reaction G:

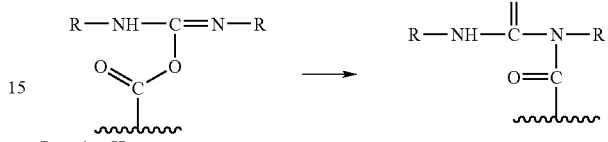

Reaction H:

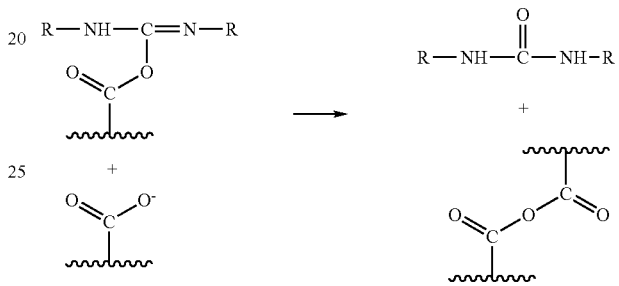

The O-acylisourea (Structure C) can be hydrolyzed as shown in Reaction F releasing the original unmodified polycarboxylate (Structure B) and the acylurea of the carbodiimide (Structure F). This is an unproductive reaction similar to reaction E, which reduces the effective concentration of the carbodiimide. The O-acylisourea, can also undergo an intramolecular rearrangement (Reaction G) to form two unreactive N-acylureas. These structures form unproductive adducts on the carboxylate molecule which cannot contribute to the peroxidase catalyzed cross-linking reaction shown (step 2 discussed below) for preparing the network according to the invention. The O-acylisourea can also react (Reaction H) with a second carboxyl group on either the same or a different polycarboxylate molecule to form an acid anhydride. This molecule can then react with Structure D to form the desired amide and regenerate the second carboxyl group. Thus there are two potential side-reactions for the O-acylisourea, which can reduce the effective concentration of the carbodiimide (Reactions F and G), and potentially lead to creation of undesired adducts on the polycarboxylate molecule.

Negative effects of these side reactions can be addressed through conventional techniques without undue experimentation.

Alternatively to the pathway shown above where the macromolecule (Structure B) is a polycarboxylate, the macromolecule can be a polyamine having multiple or periodic amine groups along its length, wherein the hydroxyphenyl groups then are provided as part of smaller carboxylic acid molecules. Suitable polyamines include: polyhexosamines such as chitosan (polyglucosamine); polyamino acids such as polylysine; polydeoxyribonucleotides such as poly (dA) (polydeoxyadenylic acid), poly(dC) (polydeoxycytidylic acid), and poly(dG) (polydeoxyguanylic acid); and polyribonucleotides such as poly(A) (polyadenylic acid), poly(C) (polycytidylic acid), and poly(G) (polyguanylic acid). The carbodiimide-mediated reaction pathway proceeds exactly as explained above to form the amide bond between the amine group and carboxylic acid group except that, as will be understood by a person having ordinary skill in the art, the resulting product will be hydroxyphenyl-substituted polyamine instead of a polycarboxylate. Other peptides and/or proteins also can be used as the macromolecules in the present invention, either which have hydroxyphenyl groups disposed along their length, or to which hydroxyphenyl groups can be provided via a substitution reaction as described herein. For example, in addition to the peptides already disclosed herein, polyarginine can be used as the macromolecule.

When substituting onto a polycarboxylate molecule, suitable hydroxyphenyl-containing compounds for use in the present invention include those having a free primary amine that can be used to modify scaffold materials having multiple or periodic $CO_2H$ groups, including tyrosine (2-amino-3-(4-hydroxyphenyl) proprionic acid) and tyramine (tyrosamine or 2-(4-hydroxyphenyl) ethylamine). When substituting onto a polyamine, suitable hydroxyphenyl-containing compounds include those having a free $CO_2H$ group that can be used to modify scaffold materials having multiple or periodic primary $NH_2$ groups, including tyrosine, 3-(4-hydroxyphenyl) propionic acid and 4-hydroxyphenylacetic acid.

The second step in preparing the cross-linked macromolecular network according to the invention is to link the resulting macromolecules, now having one or more hydroxyphenyl groups attached, via a dihydroxyphenyl linking structure. In this step hydroxyphenyl groups attached to different macromolecules are linked via the reaction mechanism shown below using a peroxide reagent in the presence of a peroxidase:

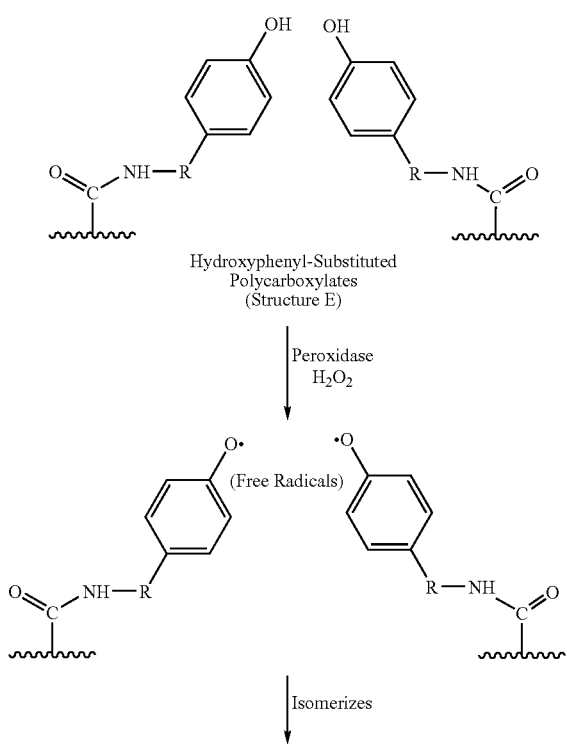

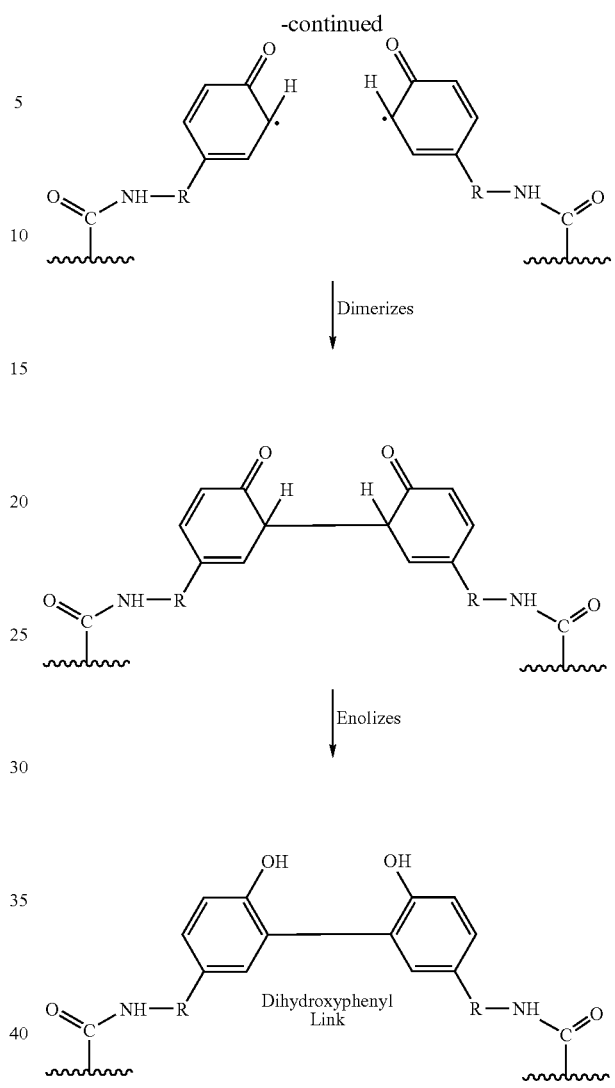

(It is noted that some dihydroxyphenyl linking may occur between different hydroxyphenyl groups on the same molecule as well). Peroxidase in the presence of a dilute peroxide (preferably $H_2O_2$) is able to extract the phenolic hydroxyl hydrogen atom from hydroxyphenyl containing compounds (such as tyramine) leaving the phenolic hydroxyl oxygen with a single unshared electron, an extremely reactive free radical. The free radical isomerizes to one of the two equivalent ortho-position carbons and then two such structures dimerize to form a covalent bond effectively cross-linking the structures, which after enolizing generates a dihydroxyphenyl dimer (a dihydroxyphenyl linkage such as dityramine linkage as described below).

For clarity, only a single dihydroxyphenyl linking reaction is shown above, but it will be understood that several or multiple such linkages will be produced when macromolecules having attached hydroxyphenyl groups are subjected to the reaction conditions (peroxide and peroxidase). Hydrogen peroxide is indicated in the above mechanism, but other suitable peroxides can be used. Also, the peroxidase preferably is horseradish peroxidase (HRP). Alternatively, any other suitable enzyme (or other agent) can be used that is capable of generating free-radicals for cross-linking scaffold materials containing hydroxyphenyl groups, preferably under ordinary metabolic conditions as described below.

The dihydroxyphenyl cross-linked macromolecular network is superior to conventional cartilage or other tissue replacement or substitution methods and products because the cross-linking reaction is enzyme driven (peroxidase). This means the cross-linking reaction is carried out under ordinary in vivo or metabolic conditions of temperature such as 35-39° C. (e.g. about 37° C.), pH range of 6-7 (e.g. about 6.5), reagents etc. (A peroxide, such as hydrogen peroxide, is the only required reagent for the cross-linking reaction). Thus, the cross-linking reaction can be performed in vivo, to provide a cross-linked hydrogel at a surgical situs, such as an orthopedic surgical situs, to promote maximum seamless integration between the hydrogel and native tissue such as bony and cartilaginous tissue. Integration of the new hydrogel scaffold with native cartilage matrix may occur immediately as the hydroxyphenyl-substituted macromolecular scaffold quickly penetrates into the existing cartilage matrix prior to cross-linking, and cross-links not only with other hydroxyphenyl-substituted macromolecular scaffold material but potentially with tyrosine residues of resident proteins in the existing cartilage matrix. This would eliminate a typical problem found with pre-formed matrix plugs, which is their poor integration into the native cartilage tissue. The ability to cross-link the hydrogel directly on the articular surface eliminates the need to surgically enlarge a defect to fit a pre-cast plug, as is necessary for hydrogels whose chemistries are toxic to or otherwise prohibit their formation inside the patient. It should be noted that most cartilage damage as a result of arthritis presents as a variable thinning of the articular surface, not holes of defined shape.

Because the cross-linking reaction requires both the peroxide and a peroxidase (preferably horseradish peroxidase), solutions containing all but one of these components can be prepared for convenient application to a surgical site. For example, a solution comprising a tyramine-(or other hydroxyphenyl containing species) substituted polycarboxylate (such as tyramine-substituted hyaluronan, etc.) and the peroxidase can be prepared, with a second solution prepared containing the peroxide. Alternatively, the peroxide and the peroxidase can be swapped between the first and second solutions, the important thing being that the peroxide and peroxidase are kept separate (i.e. in separate solutions) until the cross-linking reaction is to be carried out. Then, the first solution is applied, (e.g. to an in vivo surgical situs), and the second solution is applied or sprayed over the first, in vivo, to cause in situ cross-linking of the tyramine residues. The cross linking reaction occurs in vivo. Other combinations will be evident from the present disclosure which are within the skill of a person of ordinary skill in the art.

Furthermore, because the cross-linking reaction occurs under ordinary metabolic conditions, additional living cells, such as chondrocytes, progenitor cells, stem cells, etc., can be provided directly to a medium containing the non-cross-linked hydroxyphenyl-substituted polycarboxylates or polyamines (or polyphenols), i.e. to the first or second solution from the preceding paragraph, wherein the cell-rich medium is applied with the macromolecules to the site in vivo, and the molecules are subsequently cross-linked via addition of peroxidase and peroxide. The result is a cross-linked macromolecular network containing the desired cells dispersed within it. Such a cell-enriched network is not possible in conventional tissue replacement matrices due to the harsh conditions of temperature and pH under which they are prepared. Further, as described below in Example 5, it has been demonstrated that the cells provided to the invented matrix as described above remain viable even after cross-linking of tyramine-substituted hyaluronan (also described below) to produce a network according to the invention.

In a preferred embodiment particularly suitable for preparing synthetic cartilage as well as other synthetic or artificial tissues, the macromolecule used to produce the network according to the invention is hyaluronan or hyaluronic acid (HA), and the hydroxyphenyl group is supplied in the form of tyramine.

Figure 3:
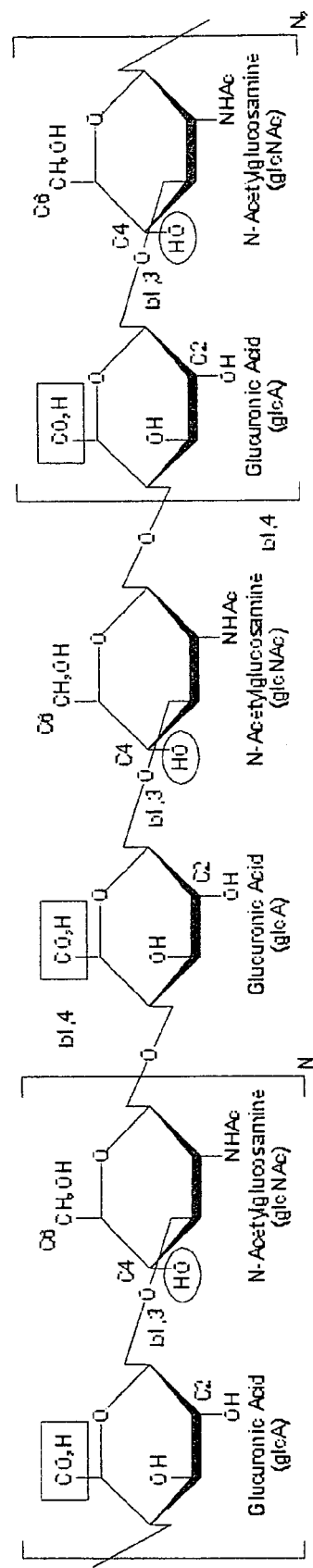
FIG. 3 is a structural formula of a hyaluronan molecule.

HA is composed of repeating pairs of glucuronic acid (glcA) and N-acetylglucosamine (glcNAc) residues linked by a β1,3 glycosidic bond as shown in FIG. 3. For each hyaluronan chain, this simple disaccharide is repeated up to 10,000 times with each repeat disaccharide linked by a β1,4 glycosidic bond. Each glcA residue has a carboxylic acid group ($CO_2H$) attached to the number S carbon atom of the glucose ring. Tyramine is a phenolic molecule having an ethyl amine group attached para to the OH group on the benzene ring. When these species are used, the mechanism for tyramine substitution onto the singly bound oxygen atom of a $CO_2H$ group on HA proceeds via the carbodiimide-mediated reaction mechanism described above as illustrated immediately below. The preferred carbodiimide species is 1-ethyl-3-(3-dimethylaminopropyl)carbodiimide (EDC) as shown.

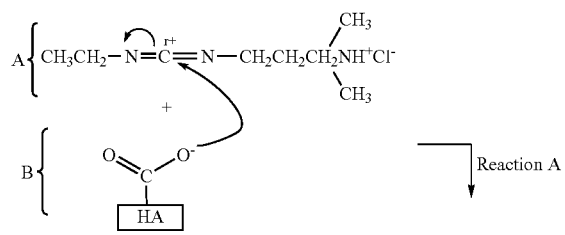

-continued

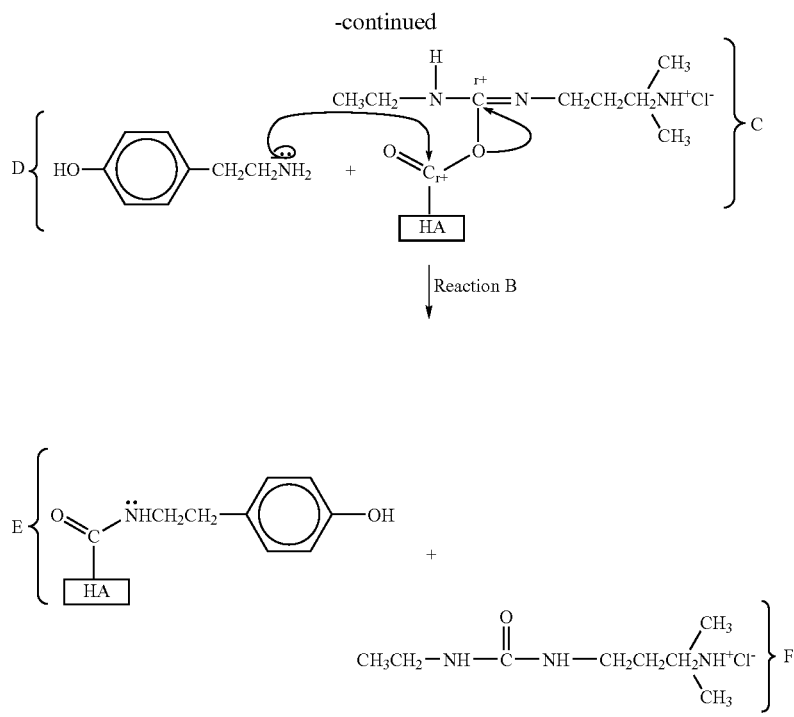

Reaction B where:
Structure A is EDC;
Structure B is hyaluronan (though only one $CO_2H$ group is shown);
Structure C is the product of Reaction A and is 1-ethyl-3-(3-dimethylaminopropyl) isourea;
Structure D is tyramine;
Structure E is tyramine-substituted hyaluronan; and
Structure F is 1-ethyl-3-(3-dimethylaminopropyl) urea (EDU).

In the above pathway, a negatively charged oxygen atom of the carboxyl group of the hyaluronan molecule attacks, via a nucleophilic reaction mechanism, the electron-deficient diimide carbon atom on the carbodiimide molecule (EDC) to form the activated O-acylisourea (Reaction A). The result is that the carbon atom of the HA carboxylate group becomes sufficiently electron deficient to be susceptible to nucleophilic attack by the unshared pair of electrons on the amine group of a tyramine molecule (Reaction B). Reaction A is preferably catalyzed by a suitable catalyst that will result in the formation of an active ester during Reaction A, thus permitting the reaction to be carried out at substantially neutral pH (e.g. pH=6.5). Suitable catalysts include N-hydroxysuccinimide (NHS), less preferably 1-hydroxybenzotriazole (HOBt) or N-hydroxysulfosuccinimide (NHSS), less preferably another suitable catalyst or combinations thereof effective to enhance the carbodiimide reaction by formation of an active ester in order to minimize the unproductive hydrolysis of carbodiimides at higher pHs. Less preferably other carbodiimides besides EDC can be used, including 1-cyclohexyl-3-[2-(4-methylmorpholino) ethyl]carbodiimide (CMC), and dicyclohexylcarbodiimide (DCC).

The result of Reaction A above is O-acylisourea-substituted hyaluronan; essentially the EDC molecule has been temporarily substituted onto the carboxylic acid group of a glcA residue from the HA molecule, making the carbon atom of the carboxylic acid group slightly positively charged. The electron pair from the terminal amine group of a tyramine molecule is then substituted onto the carbon atom via a nucleophilic substitution reaction as explained in the preceding paragraph (Reaction B). The result of Reaction B is the tyramine-substituted HA molecule (T-HA) and acylurea, a byproduct. It will be understood that Reactions A and B will result in a plurality of tyramine substitutions on the periodic glcA residues of HA molecules; a single substitution has been shown here for brevity and clarity.

After formation of T-HA, a plurality of T-HA molecules are reacted via peroxide and peroxidase enzyme to cross-link T-HA molecules as previously described and illustrated above. That is, the hydroxyphenyl groups on the tyramine residues now attached to HA molecules react with peroxide (preferably $H_2O_2$) in the presence of a peroxidase to remove the phenolic hydrogen atom resulting in a tyramine free radical, with the unpaired electron associated with the phenolic oxygen atom. This free radical species isomerizes or resonates, resulting in a resonance structure (or free radical isomer) with the unpaired electron now associated with an ortho carbon atom on the phenolic ring. In this position, the unpaired electron quickly reacts with a similarly situated unpaired electron on another tyramine free radical to form a covalent bond therebetween. The result is a free-radical driven dimerization reaction between different tyramine free radical residues attached to different glcAs of the same or different HA molecules. This dimerized species further enolizes to restore the now-linked tyramine residues, resulting in a dityramine linkage structure. It will be understood that a plurality of reactions as herein described will occur between adjacent tyramine residues, resulting in a cross-linked macromolecular network of T-HA molecules according to the invention having the following cross-linking structure:

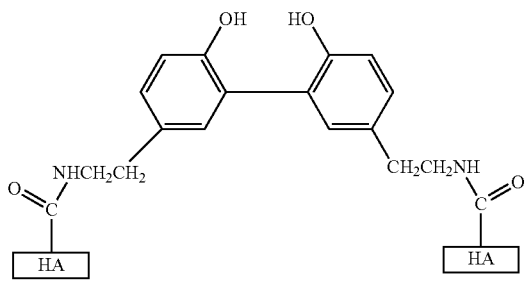

The cross-linked T-HA network can be provided with aggrecan molecules in a conventional manner, e.g. via link proteins, to provide a cross-linked T-HA network having aggrecan molecules attached to the HA chains. Thus, a network similar to that found in a normal cartilage aggregate can be provided according to the invention, with the dityramine bonds holding the network together thereby constraining the contained aggrecan network, instead of collagen fibrils as in normal cartilage.

It will be understood from the present invention that other glycosaminoglycans, polysaccharides and polycarboxylic acids can be used as the macromolecules for producing the cross-linked network disclosed herein. For example, suitable glycosaminoglycans, other than HA, include chondroitin, chondroitin sulfate, dermatan sulfate, heparan sulfate and heparin. Other suitable polycarboxylates include: proteoglycans such as versican, aggrecan, and cartilage aggregates composed of aggrecan, hyaluronan and link protein; polyuronic acids such as polypectate (polygalacturonic acid), polyglucuronic acid, pectin (polygalacturonic acid methyl ester), colominic acid (poly[2,8-(N-acetylneuraminic acid)]), and alginate (poly[mannuronate-co-guluronate]); and amino acids (having at least 2 amino acid units) that meet the definition of polycarboxylate given above, such as polyaspartic acid, and polyglutamic acid. All of these can be substituted with one or a plurality of hydroxyphenyl groups using the carbodiimide-mediated reaction pathway disclosed herein by a person of ordinary skill in the art without undue experimentation.

As mentioned above, it is also to be understood that native polyphenol compounds, which already contain two or more hydroxyphenyl groups that can be cross-linked using the described enzyme catalysis chemistry can be used in place of the polycarboxylates and polyamines described above which must have the hydroxyphenyl groups added by a chemical reaction.

In another preferred embodiment, a network of tyramine cross-linked chondroitin sulfate molecules (either alone or provided as part of aggrecans) is provided to simulate or replace normal cartilage. Chondroitin sulfate is identical to hyaluronan except: 1) the repeat disaccharide structure contains N-acetylgalactosamine (galNAc) rather than glcNAc, a difference in only the position of the hydroxyl group attached to the 4-carbon (circled in FIG. 3); 2) the presence of O-sulfation on the hydroxyl groups at the 4-and/or 6-position of the galNAc residue and/or the 2-position of the glcA residue (FIG. 3); and 3) the size of the chondroitin sulfate chains, which are smaller than hyaluronan with between 20 to 100 repeating disaccharide units. (An aggrecan molecule is made up of multiple-roughly 100 chondroitin sulfate chains linked to a core protein through a linkage saccharide located at each chain's reducing end). In this embodiment, the negatively charged $SO_4^{2-}$ groups of adjacent (cross-linked) chondroitin sulfate molecules provide the principal repulsive force contributing to the compression resistance of the network aggregate while the tyramine cross-links constrain the chondroitin sulfate network from breaking or dissipating. The result is a similarly non-displaceable chondroitin sulfate network (and concomitant water-impermeability) as in normal cartilage, but without the extracellular collagen fibril matrix or the HA chains found in normal cartilage. In fact, by directly cross-linking chondroitin sulfate molecules, (instead of their core HA molecules as in the previously described embodiment), the repulsive force between adjacent chondroitin sulfate molecules may be strengthened, resulting in even stronger fluid flow resistance compared to normal cartilage. This may result in greater loading force absorption and dissipation capacity than normal cartilage because the interstitial fluid phase is even more constrained from flowing. In this embodiment, where chondroitin sulfate molecules are directly cross-linked, certain cartilage degenerative conditions are entirely circumvented; e.g. conditions where the core protein to which chondroitin sulfate molecules are ordinarily bonded in normal cartilage becomes cleaved between the HA binding domain (G1) and the second globular domain (G2) thus allowing the chondroitin sulfate rich region to diffuse out from the cartilage aggregate. In this embodiment, because the chondroitin sulfate molecules are directly cross-linked to one another, unassociated with an aggrecan or other proteoglycan molecule, they cannot be cleaved or carried away as in normal cartilage.

Nonetheless, a tyramine cross-linked T-HA network (having an HA backbone chain with attached aggrecan molecules, which in turn include chondroitin sulfate chains) may be preferred because of the high availability of HA. This may be beneficial in the case of cartilage replacement or repair using the present invention, because the body's normal metabolic pathway for generating cartilage may be able to build directly onto an implanted tyramine cross-linked T-HA network as will be described.

The dityramine cross-linked T-HA network described above has particular utility for producing artificial or synthetic cartilage. Cartilage implants are frequently used in reconstructive procedures of the head and neck to repair cartilaginous or bony defects secondary to trauma or congenital abnormalities. Applications specific to the ear include otoplasty and auricular reconstruction, which are often undertaken to repair cartilaginous defects due to trauma, neoplasm (i.e., squamous cell carcinoma, basal cell carcinoma, and melanoma), and congenital defects such as microtia. Applications specific to the nose include cosmetic and reconstructive procedures of the nose and nasal septum. Dorsal hump augmentation, tip, shield and spreader grafts are frequently used in cosmetic rhinoplasty. Nasal reconstruction following trauma, neoplasm, autoimmune diseases such as Wegeners granulomatosis, or congenital defects require cartilage for repair. Septal perforations are difficult to manage and often fail treatment. Cartilage grafts would be ideal for these applications, though autologous or donor cartilage often is unavailable. Applications specific to the throat include laryngotracheal reconstruction, which in children usually requires harvesting costal cartilage, which is not without morbidity. Auricular and septal cartilage is often inadequate for this application. Therefore engineered cartilage from the cross-linked HA networks as described herein can have significant impact on the management of these problems. Laryngotracheal reconstruction is usually performed for airway narrowing due to subglottic or tracheal stenosis. The etiology may be traumatic (i.e., intubation trauma, or tracheotomy) or idiopathic.

Other possibilities include chin and cheek augmentation, and use in ectropion repair of the lower eyelid, in addition to numerous cranio facial applications. It should be noted that these applications may not need cartilage with the exacting mechanical properties of articular cartilage. Inclusion of a cell population or bioactive agents may also be desirable.

One particular application where a cross-linked network according to the invention will have substantial utility is in the production of an artificial kidney. The kidney filters blood by two mechanisms: one is by size exclusion and the second is by charge exclusion. MEMS devices have been designed for use in artificial kidney devices, which contain precisely defined micropores that can effectively mimic only the size exclusion characteristics of the kidney. In a healthy kidney, the charge exclusion related filtration is the result of heparan sulfate proteoglycans present in a basement membrane, which separates two distinct cell types important for other kidney related functions. To mimic this charge barrier in the MEMS engineered artificial kidney, hydrogels can be prepared composed of either heparan sulfate or heparin that are cross-linked via dihydroxyphenyl (dityramine) links as described herein and provided within the pores of the MEMS device. This heparin/heparan sulfate hydrogel can then be sandwiched between two hyaluronan derived hydrogels (e.g. T-HA described above) as described herein, and containing one of each of the cell types normally found in a normally functioning kidney. The central heparin/heparan sulfate hydrogel provides the charge exclusion properties for the device. The outer two hyaluronan hydrogel layers provide protection from the immune system and fouling by normal cellular and molecular debris. Inclusion of the two cell types on opposite sides of the filtration barrier provides a cellular component in its normal physiologic orientation.

In another promising application, the hydrogels according to the invention can be applied in developing an artificial pancreas. A problem in development of an artificial pancreas is the short half life of MEMS engineered glucose sensors due to fouling of the detector electrode in vivo. Coating of the surface of these detectors with a hyaluronan hydrogel (e.g. T-HA) as described herein would permit diffusion of the small molecular weight glucose molecules that they are designed to detect while providing protection from the immune system and fouling by normal cellular and molecular debris.

In summary, it will be evident from the foregoing that macromolecules useful as scaffold materials for formation of hydrogels include but are not limited to polycarboxylates (containing free carboxylate groups), polyamines (containing free primary amine groups), polyphenols (containing free hydroxyphenyl groups) and their copolymers, examples of which have been described above. When polyphenols are used, the first step in preparing the network according to the invention described above can be omitted because polyphenols already contain multiple or periodic hydroxyphenyl groups. Otherwise, both polycarboxylates and polyamines must have hydroxyphenyl groups added or substituted along their length, preferably via the above-described carbodiimide reaction pathway. The second step in preparing the network is to carry out an enzyme driven dimerization reaction between two hydroxyphenyl groups attached to adjacent macromolecules (whether polycarboxylates, polyamines or polyphenols) in order to provide a cross-linked structure. This step is carried out using a peroxide reagent (preferably hydrogen peroxide) in the presence of a suitable enzyme (preferably HRP) under metabolic conditions of temperature and pH.

In the case of the preferred dityramine cross-linked T-HA network, in the first step the carboxyl groups on high molecular weight hyaluronan (HA) are substituted with tyramine which introduces reactive hydroxyphenyl groups into the HA molecule. This tyramine substitution reaction preferably is mediated by the carbodiimide, 1-ethyl-3-(3-dimethylaminopropyl)carbodiimide (EDC) with the degree of tyramine substitution on HA controlled by the molar ratios and absolute concentrations of tyramine, EDC and HA used in the reaction mix. Excess reagents such as unused tyramine and EDC are subsequently removed by dialysis, allowing isolation and recovery of high molecular weight tyramine-substituted HA (T-HA). The percent tyramine substitution within each T-HA preparation is easily calculated by measuring: 1) the concentration of tyramine present in the preparation, which is quantitated spectrophotometrically based on the unique UV-absorbance properties of tyramine at 275 nm (see Example 2 below); and 2) the concentration of total carboxyl groups in the HA preparation, which is quantitated spectrophotometrically by a standard hexuronic acid assay. By this technique, T-HA preparations which contain a percent tyramine substitution of only 4-6% have been routinely synthesized experimentally. At this level of tyramine substitution, the vast majority (preferably at least 60, 70, 80, 90, or 95, percent) of the HA molecule remains chemically unaltered, and therefore biologically functional. From this formulation of T-HA (i.e. 4-6% tyramine substitution) a wide range of biomaterials with a wide range of physical properties can be produced by simply varying the concentration of the T-HA used in the second step of the process.

In the cross-linking reaction, solutions of T-HA are cross-linked to form hydrogels through an enzyme (peroxidase) driven reaction, which catalyzes the formation of a covalent bond between two tyramine adducts on adjacent HA molecules, producing a single dityramine cross-link. The formation of hundreds of these dityramine cross-links per HA molecule result in formation of a stable 3-dimentional scaffold or hydrogel. Addition of very dilute peroxide (preferably $H_2O_2$) is required to initiate the cross-linking reaction as it is the peroxide, not -HA, that is the actual substrate for the peroxidase enzyme. The products of the reaction of the peroxidase enzyme on peroxide are free radicals that are preferentially taken up by the hydroxyphenyl rings of tyramine resulting in the formation of the dityramine cross-links. The dityramine linked structures are fluorescent blue (see Example 2), a property which is used to both image the hydrogels and to quantify the degree of cross-linking within the hydrogels. Since the cross-linking reaction is enzyme driven, the hydrogels can be formed under physiologic conditions, and therefore can be formed in the presence of included cells or bioactive agents, or directly adjacent to living tissue while maintaining cell and tissue viability.

The resulting hydrogels are optically clear with a wide range of physical properties depending on the initial T-HA concentration. For example, hydrogels formed from T-HA solutions of 6.25, 12.5, 25, 50 and 100 mg/ml T-HA have been shown experimentally to have physical properties (rigidity, rheology and texture) of a jelly, a gelatin, a dough, a resilient rubber-like composition (similar to a rubber ball), and a cartilage-like material respectively-see Example 3. These materials have potential applications in a wide range of clinical settings including tissue engineering of both orthopedic (i.e. cartilage, bone, tendon, meniscus, intervertebral disk, etc.) and non-orthopaedic (kidney, liver, pancreas, etc.) tissues, gene and drug delivery, coating of non-biological devices for in vivo implantation (i.e. glucose sensors, artificial hearts, etc.), wound repair, biosensor design, and vocal chord reconstruction.

Advantageous properties of the hydrogels described herein include the ability to: 1) provide easy characterization and quality control; 2) integrate with existing tissue matrices; 3) directly incorporate into newly formed matrices; 4) directly include cells and bioactive factors; 5) maintain biocompatibility; 6) control bioresorption; 7) cast easily into complicated anatomical shapes (see Example 6 below); and 8) exhibit the mechanical properties of native tissues such as articular cartilage.

Further aspects of the invention will be understood in conjunction with one or more of the following examples, which are provided by way of illustration.

EXAMPLES

Example 1

Experimental quantities of tyramine-substituted hyaluronan hydrogels having dityramine cross-links according to the invention have been prepared as follows. HA is dissolved at 1 mg/ml based on hexuronic acid in 250 mM 2-(N-morpholino)ethanesulfonic acid (MES), 150 mM NaCl, 75 mM NaOH, pH 6.5 containing a 10-fold molar excess of tyramine relative to the molar concentration of HA carboxyl groups. Tyramine substitution onto the carboxyl groups is then initiated by the addition of a 10-fold molar excess of EDC relative to the molar concentration of the HA carboxyl groups. A 1/10th molar ratio of N-hydroxysuccinimide (NHS) relative to the molar amount of EDC is added to the reactions to assist the EDC catalyzed amidation reaction by formation of active esters. Reactions are carried out at room temperature for 24 hours, after which the macromolecular fraction is recovered from unreacted small molecular weight reactants such as tyramine, EDC, NHS, and MES by exhaustive dialysis versus 150 mM NaCl and then ultrapure water followed by lyophilization. After lyophilization, the tyramine-substituted HA (T-HA) product is dissolved to working concentrations of between 5 and 100 mg/ml in PBS (which is a buffer compatible with cell suspension, in vivo tissue contact, and the cross-linking reaction) to provide various concentration preparations depending on the desired rigidity of the final hydrogel. Alternatively, the solvent can be any other suitable solvent besides PBS that will not substantially negatively impact the enzyme activity and that will not interfere with cross-linking reaction via selective uptake of free radicals generated by the enzyme. Suitable alternative solvents include water, conventional biological tissue culture media, and cell freezing solution (generally composed of about 90% blood serum and about 10% dimethyl sulfoxide). Prior to suspension of cells (see Example 5) or contact with tissues in vivo, the T-HA should be filtered through a 0.2 μm filter. Next, tyramine-tyramine linking is carried out by adding 10 U/ml of type II horseradish peroxidase (HRP) to each T-HA preparation. Cross-linking is initiated by the addition of a small volume (1-5 μl) of a dilute hydrogen peroxide solution (0.012%-0.00012% final concentration) to yield the final hydrogel with desired rigidity. For preparation of larger quantities or volumes of a desired hydrogel, quantities of reagents provided in this paragraph could be scaled up appropriately by a person of ordinary skill in the art.

Example 2

An experiment was conducted to determine the degree of tyramine substitution (and consequent dityramine cross-linking) for a T-HA macromolecular network according to the invention. Initially, three formulations of (uncrosslinked) tyramine-substituted hyaluronan (T-HA) were prepared as described above, designated 0x, 1x or 10x. The 0x formulation was prepared using no EDC (i.e. containing no carbodiimide), meaning there was no carbodiimide present to mediate the reaction for creating an amide bond between the $NH_2$ group on tyramine and a $CO_2H$ group on the HA molecules. Thus, the 0x formulation can be considered a control. The 1x formulation contained a 1:1 stoichiometric ratio of EDC based on the quantity of $CO_2H$ groups present on the HA molecules in the reaction mixture. The 10x formulation contained a 10:1 stoichiometric ratio (or 10-fold excess) of EDC based on the quantity of $CO_2H$ groups present on the HA molecules in the reaction mixture. In all three formulations, a stoichiometric excess of tyramine was provided relative to the quantity of $CO_2H$ groups on HA. In all three formulations (0x, 1x and 10x) the reactants and the appropriate amount of EDC for the formulation were combined in a vial and agitated to facilitate the tyramine-substitution reaction. All three formulations were allowed to react for 24 hours at room temperature, after which the vial contents were dialyzed to remove unreacted tyramine molecules, EDC and acylurea (EDU) byproducts of the reaction. These molecules were easily separated from HA and any formed T-HA molecules through dialysis due to the relatively small size of tyramine, EDC and EDU compared to macromolecular HA. Once unreacted tyramine and EDC were removed, the remaining contents for each formulation were analyzed to determine the rate of tyramine substitution relative to the total number of available $CO_2H$ sites present on HA molecules.

Tyramine exhibits a UV absorbance peak at 275 nm, making the degree of tyramine substitution easily detectable against a tyramine calibration curve. Based on UV-spectroscopic analysis of the above three T-HA formulations, it was discovered that the HA-tyramine substitution reaction carried out with no EDC present (formulation 0x) resulted in substantially zero tyramine substitution onto the HA molecules. This confirmed the importance of using a carbodiimide reaction pathway in the tyramine substitution reaction. However, the tyramine absorption in the T-HA formulation prepared using a 1:1 EDC:$CO_2H$ stoichiometric ratio in the tyramine substitution reaction (formulation 1x) resulted in a tyramine substitution rate of about 1.7% relative to all available $CO_2H$ groups on the HA chains. The 10x formulation (10:1 EDC:$CO_2H$ ratio) resulted in about a 4.7% substitution rate.

Subsequently, hydrogen peroxide and horseradish peroxidase (HRP) were added to each of the three dialyzed HA/T-HA formulations (0x, 1x and 10x) at 5 mg/mL and the resulting formulations were allowed to react to completion. After reaction in the presence of peroxide and HRP, it was observed that the 0x formulation remained entirely liquid, having a strong meniscus; no gel formation was observed, confirming the fact that no or substantially no tyramine substitution had occurred when no EDC was used in the tyramine substitution reaction. For the 1x formulation, only a very weak meniscus was observed and the contents of the vial had gelled, confirming that both tyramine substitution and cross-linking had occurred. For the 1x formulation, a relatively rigid gel had formed, and in fact had shrunk relative to the initial volume of fluid in the container, leaving a quantity of liquid (having a meniscus) on top. The gel prepared from the 10× formulation (having a 4.7% tyramine substitution rate) was much firmer and more rigid than that from the 1× formulation having a 1.7% tyramine substitution rate.

The dityramine structure exhibits a blue fluorescence on exposure to UV light. The products of each of the above formulations were exposed to UV light to detect the presence of dityramine cross-links. As expected, both the 1× and 10× hydrogels exhibited blue fluorescence (the 10× hydrogel fluorescence being more intense than that of the 1× hydrogel), while the 0× formulation exhibited no blue fluorescence at all. This confirmed the presence of dityramine cross-links in both hydrogels, and that the occurrence of dityramine in the more rigid hydrogel (10×) was greater than in the less rigid hydrogel (1×).

The overall result was that the importance of the carbodiimide-mediated reaction pathway was demonstrated, and it was confirmed that the relative rigidity of a hydrogel formed from a cross-linked T-HA network according to the invention is proportional to the degree of dityramine cross-linking, which is in turn proportional to the degree of tyramine-substitution onto HA. It was quite a surprising and unexpected result that even a 1.7% tyramine-substitution rate (and subsequent cross-linking rate to form dityramine links) provided a suitably firm T-HA gel (or hydrogel) according to the present invention. A 4.7% substitution (and cross-linking) rate resulted in even a firmer T-HA gel. Also surprising was that a ten-fold stoichiometric excess of carbodiimide (EDC) relative to the quantity of carboxylic acid groups present in the reaction mixture (formulation 10×) resulted in only about a 4.5-4.7% tyramine substitution rate, yet stable and cohesive tyramine cross-linked T-HA networks were nonetheless achieved.

This means that the majority of the carboxylic acid groups on the HA molecules are unsubstituted and not tyramine cross-linked, essentially remaining the same as in the native HA molecule, yet the resulting network is a cohesive and stable hydrogel. Therefore, when used as a cartilage substitute in vivo, because a majority of the HA molecules in the invented T-HA network or gel are essentially unaltered compared to HA in normal cartilage, it is believed that the body's native metabolic pathways (aided or unaided by cells provided within the T-HA network) may recognize the invented network as native biologic material, and will be able to carry out ordinary synthesis and metabolism functions with respect thereto. In addition, it is noted that HA is a highly ubiquitous material in the body, and is non-immunogenic in humans. As a result, it is believed the invented cross-linked macromolecular network, comprised a majority of unaltered native HA, will have substantial application in a wide variety of tissue engineering applications where it is desirable or necessary to provide synthetic tissue in a human body. This represents a significant advance over the state of the art. Therefore, quite surprisingly, a high degree of tyramine substitution, e.g. greater than about 10-20%, may be undesirable; the above described experiments demonstrated that such high degrees of substitution are unnecessary to provide a suitable T-HA network. Preferably, a dihydroxyphenyl (e.g. dityramine) cross-linked polycarboxylate (e.g. HA) network according to the invention has a hydroxyphenyl (tyramine) substitution rate of less than 50, preferably less than 40, preferably less than 30, preferably less than 20, preferably less than 15, preferably less than 10, preferably less than 9, preferably less than 8, preferably less than 7, preferably less than 6, preferably less than 5, percent based on the total quantity of $CO_2H$ groups present on the polycarboxylate (HA) molecules.

Example 3

Conventionally, it has been believed that natural cartilage exhibits its viscoelastic properties and its ability to resist deformation and absorb compressive loads principally as a result of the repulsive forces between negatively charged $SO_4^{2-}$ groups on adjacent chondroitin sulfate chains present in the aggrecan matrix. An experiment was performed to determine the efficacy of a macromolecular network according to the invention consisting only of dityramine cross-linked hyaluronan molecules (i.e. no aggrecan or chondroitin sulfate) to resist deformation and absorb compression compared to natural cartilage despite the absence of $SO_4^{2-}$ groups. A formulation of uncross-linked T-HA was prepared and purified as in Example 1 having a tyramine substitution rate of about 5%. From this T-HA formulation, five different T-HA concentrations were prepared:

Concentration 1: 6.25 mg T-HA/mL PBS
Concentration 2: 12.5 mg T-HA/mL PBS
Concentration 3: 25 mg T-HA/mL PBS
Concentration 4: 50 mg T-HA/mL PBS
Concentration 5: 100 mg T-HA/mL PBS Each of the above preparations was then reacted in the presence of hydrogen peroxide and horseradish peroxidase, also as in Example 1, to form dityramine cross-links between the T-HA molecules and provide respectively Hydrogels 1, 2, 3, 4 and 5. Each of these five hydrogels was found, surprisingly and unexpectedly, to be a stable and substantially coherent material with the physical properties of each hydrogel varying relative to the concentration of T-HA in the preparation from which it was made. For example, qualitatively Concentration 1 resulted in Hydrogel 1 having rigidity and rheological properties comparable to that of Vaseline or jelly; the hydrogel was stable and coherent yet could be caused to flow or spread on application of an external force, e.g. from a spatula or other conventional tool. Hydrogel 1 exhibited excellent adhesive properties making it an ideal candidate for a nonallergenic coating material for surgical instruments during surgery, e.g. ophthalmologic surgery. Hydrogel 2 was more rigid than Hydrogel 1 due to the greater concentration of T-HA in the preparation from which it was made, and the consequent predicted decrease in intramolecular cross-linking and increase in intermolecular cross-linking associated with increased T-HA concentration. Hydrogel 2 exhibited Theological and rigidity properties characteristic of gelatins, with a degree of viscoelastic reboundability on external loading. On greater loading, Hydrogel 2 was found to break up into smaller pieces instead of flowing, also characteristic of a gelatinous material. Hydrogel 3 had the properties and consistency of a dough or malleable paste, also not flowing on application of an external loading force. This material also exhibited substantially greater viscoelastic properties compared to Hydrogels 1 and 2. Hydrogel 4 was a highly rigid and coherent gel that strongly resisted breaking up on application of an external loading force. Hydrogel 4 was a highly resilient rubber-like composition that actually generated substantial springing force upon sudden compression (e.g. dropping onto the floor). This ability of Hydrogel 4 to generate such a springing force in response to a sudden compression may make this material ideal for certain joint replacement/repair applications where the joint undergoes repeated and periodic compressional loading (e.g. the ankle joint). In addition to the properties described for Hydrogel 4, Hydrogel 5 had cartilage-like properties with both the appearance of articular cartilage and the feel of cartilage upon cutting with a surgical blade.

Confined compression tests were performed to quantitatively determine the compressive mechanical properties of the five different hydrogels described above. A custom built polycarbonate confining chamber, and porous polypropylene filter platen (20 μm pores, 20% porosity) were used to perform the confined compression testing. Five cylindrical plugs (7.1 mm in diameter, approximately 3 mm in thickness) at each hydrogel concentration were made using the confining chamber and the freeze-thaw technique described in Example 4 below. The following testing protocol was followed for a series of stress relaxation tests in confined compression. All testing was performed using an Instron 5543 machine under computer control, which recorded the time-displacement-load data at a frequency of 10 Hz. A ±5 N or ±50 N load cell (Sensotec) was used to monitor load throughout each test. A step of 30 μm (30 μm/sec), representing 1% strain, was applied until the sample reached equilibrium. This was defined as a relaxation rate that slowed to less than 10 mN min$^{-1}$, at which time the next step was automatically started, until 20 cycles (representing approximately 20% strain) were completed. The thickness of each sample tested in confined compression was determined mechanically, by measuring the displacement at which the compressive response initiated relative to the bottom of the chamber as measured with the Instron 5543 machine. The measured thickness was used to calculate the strain percentage for each step.

Figure 4:
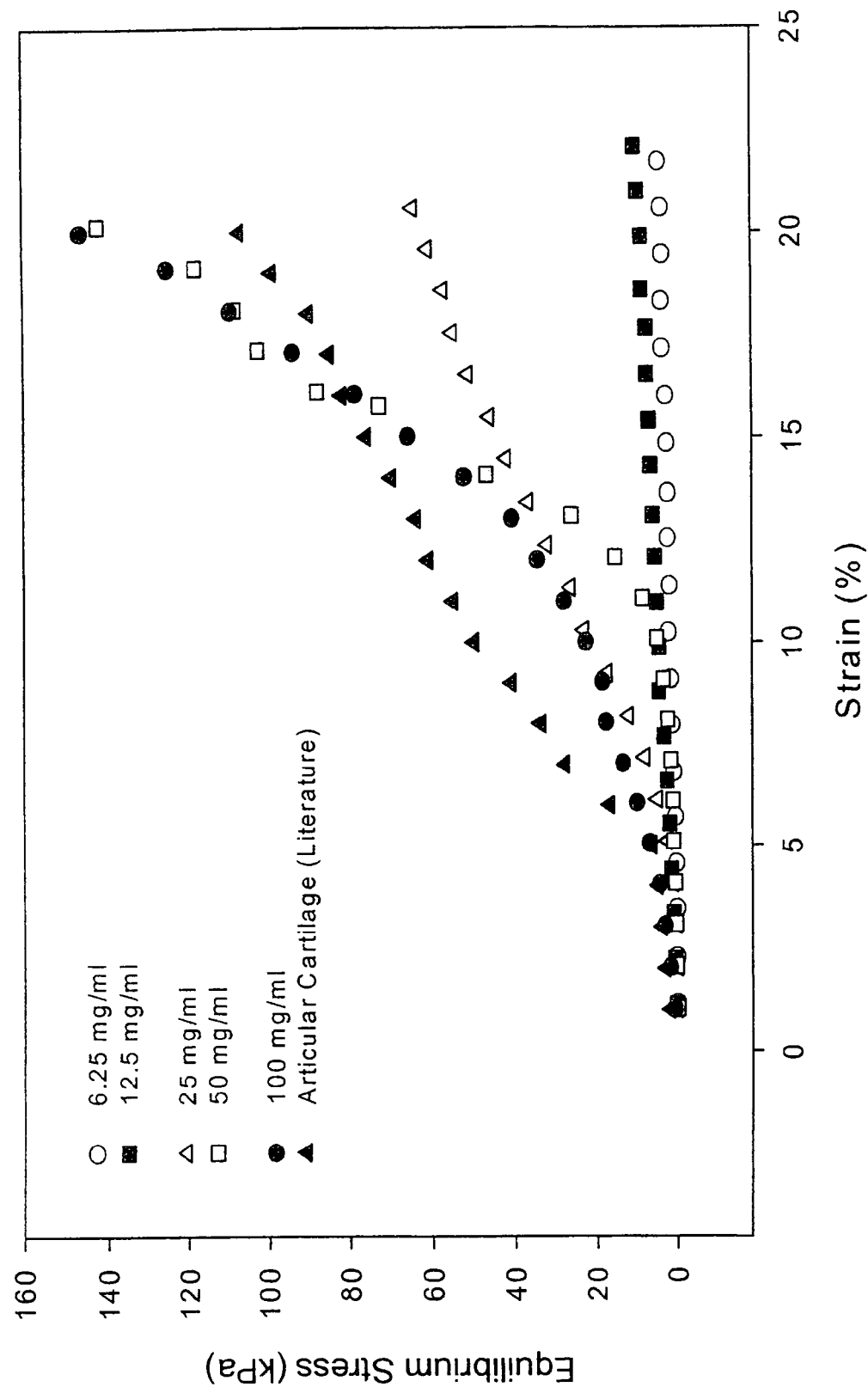
FIG. 4 is a graph showing comparative results for mechanical testing in a confined compression test (equilibrium stress versus applied strain) of T-HA hydrogels according to the invention versus published results for articular cartilage plugs (Example 3).

The compressive mechanical properties of the five hydrogels were determined as described in the preceding paragraph. Load data was normalized by sample cross-sectional area (39.6 mm$^2$) to compute stress. The equilibrium stress was plotted against the applied strain for each material formulation. The aggregate modulus at each step was defined as the equilibrium stress divided by the applied strain. For each material, the aggregate modulus was defined as the slope of the equilibrium stress-strain data in the most linear range. The results for the confined compression tests are shown in FIG. 4. All five hydrogels were testable in confined compression, and demonstrated characteristic stress relaxation responses typical of biphasic materials (such as cartilage). The aggregate moduli for the 6.25 mg/ml and 12.5 mg/ml T-HA hydrogels were 1-2 orders of magnitude lower than articular cartilage. The 25 mg/ml T-HA hydrogel displayed an aggregate modulus of approximately half of the reported values for articular cartilage. The 50 and 100 mg/ml T-HA hydrogels displayed aggregate moduli, which over the linear range were less than reported values of articular cartilage, but which had moduli that were larger than articular cartilage at strains of 15-20%. These data demonstrate the ability to characterize hydrogels using standard mechanical assays, and generate hydrogels with similar mechanical properties to that of articular cartilage.

Based on the above experiments it was surprisingly and unexpectedly discovered that a dityramine cross-linked hyaluronan network will produce a coherent hydrogel material whose rigidity and other physical (rheological) properties can be tuned by varying the T-HA concentration prior to cross-linking the tyramine groups to suit a particular application. The coherence and elastic properties of these hydrogels was observed even absent any (or substantially any) $SO_4^{2-}$ groups in the network to supply the charge-to-charge repulsive forces to generate the material's compression resistance and elasticity. This was a highly surprising and unexpected result that may have substantial positive consequences in tissue engineering applications. Hyaluronan is a highly ubiquitous and non-immunogenic molecule found in humans. Therefore, hydrogels consisting of dityramine cross-linked hyaluronan networks may provide very suitable tissue replacement materials that can be implanted within a human body, whose rigidity can be tuned based on the application. As these materials will be composed of predominantly unaltered hyaluronan which is non-immunogenic, and it is believed may result in zero or substantially zero immune response. This is an important advantage over many conventional tissue engineered materials whose formation chemistries prevent their application in vivo due to harsh reaction conditions or reagents, and whose final chemical structures are more likely to induce an immune response.

Example 4

A number of methods of preparing hydrogels such as those described in Example 3 have been developed to cast or form the hydrogel into a predetermined three-dimensional shape. This is important for myriad tissue engineering applications where it is necessary to provide artificial tissue material to fill a native tissue defect or void within a patient.

A first method is to employ an in situ forming technique where the hydrogel is formed in place, i.e. in position and in the shape of its final application and structure. The in situ formation method has been carried out experimentally as follows. Tyramine-substituted hyaluronan (T-HA) was prepared via the carbodiimide-mediated pathway described herein. Following dialyzation to remove unreacted tyramine, EDC, NHS, etc., and dissolution at the desired concentration in PBS (see Example 1 above), a small quantity of horseradish peroxidase enzyme was added to the T-HA liquid preparation to form a first solution. This first solution was provided into a laboratory container (to simulate an in vivo situs) having a specific interior geometry. Subsequently, a second solution was prepared containing very dilute hydrogen peroxide (0.012%-0.00012% final concentration). A small volume of this second solution relative to the first solution was then injected into the container already containing the first solution to initiate the dityramine cross-linking reaction to yield the hydrogel. Hydrogels prepared by this technique have been prepared having varying rigidity and rheological properties as described above in Example 3, and conformed well to the interior surface contour of the container in which they were formed. Because the principal reagents ($H_2O_2$ hyaluronan and peroxidase) are either non-allergenic or diffusible molecules, and because the cross-linking reaction proceeds under metabolic conditions of temperature and pH, this technique can be performed in vivo at a surgical situs in a patient as a surgical procedure to produce a defect-conforming hydrogel. This method is particularly attractive for reconstructive facial surgery in which the uncross-linked T-HA preparation (with peroxidase) can be injected and manipulated subcutaneously by the surgeon to produce the desired facial contours and then the hydrogel subsequently cross-linked by injection of a small volume of the hydrogen peroxide solution.

A second method is a porous mold technique and is suitable for forming hydrogels into more complex three-dimensional structures. In this technique a porous hollow mold is first cast conforming to the shape and contour of the intended final structure. For illustration, a mold can be prepared having an interior surface in a cuboid shape if a cuboid shaped hydrogel were desired. The mold can be prepared or cast via conventional techniques from conventional porous materials, e.g. plaster of paris, porous or sintered plastics or metals, etc. In a particularly preferred embodiment the mold is prepared using a cellulosic dialysis membrane. The first and second solutions are prepared as above, and the first solution is provided into the hollow mold cavity of the porous mold. Subsequently, the now-filled mold is submersed in a bath of very dilute peroxide. The macromolecular T-HA and peroxidase molecules are unable to diffuse out of the porous mold due to their size, however the very small peroxide molecules ($H_2O_2$) are able to diffuse in and react in the presence of the peroxidase enzyme to yield dityramine cross-links. It is inherent in this method that cross-linking occur from the outside inward to produce the finished hydrogel shape, and a certain degree of trial and error may be required to determine optimal or sufficient immersion times in the peroxide bath. Determination of these time periods is within the skill of a person having ordinary skill in the art. Successfully completed three-dimensional hydrogel shapes have been prepared in laboratory bench experiments via this porous mold technique.

A third method is a freeze-thaw technique that is suitable for casting hydrogels according to the invention in highly intricate predetermined three-dimensional shapes, e.g. having internal folds such as a human ear. In this technique, a mold is prepared from a soft or malleable material such as a polymeric material having a low glass transition temperature, e.g. below −80° C. The preferred mold materials are silicones having low glass transition temperatures, such as polydimethylsiloxane whose glass transition temperature is about −127° C., however other suitably low glass transition (e.g. below −80° C.) silicones, as well as other polymers, can be used. The silicone (preferred material) is first prepared such that it has an inner mold cavity conforming to the surface shape, contour and volume of a desired hydrogel part via any conventional or suitable technique (i.e. press-molding, carving, etc.). First and second solutions are prepared as above, and the first solution is provided into the inner mold cavity of the silicone mold. The now-filled silicone mold is then cooled to about −80° C. by contacting with solid $CO_2$ (dry ice). Because the first solution is principally water, it freezes into a solid ice form conforming to the shape and contour of the inner mold surface. However, the silicone mold, having a glass transition temperature below −80° C., remains soft and malleable and the solid ice form of the first solution is easily removed. Because the first solution expands as it freezes, suitable mechanical hardware should be used to ensure the silicone mold does not deform or expand as the solution freezes. Preferably, port holes are provided in the mold to allow for expansion and discharge of the first solution as it expands during the freezing process.

Once the solid ice form of the first solution has been demolded, minute defects or flaws in the three-dimensional structure can be repaired by carving with a suitable tool, and more of the liquid first solution can be added to fill surface voids, which liquid instantly freezes on contact with the solid ice form. Also, the ice form can be placed back on the dry ice surface if desired to ensure uniform temperature and freezing of any added first solution material. Once the three-dimensional shape of the ice form has been perfected, it is immersed in a liquid peroxide solution to initiate thawing of the frozen water and dityramine cross-linking from the outside-in. This is possible do to the rapid kinetics of the cross-linking reaction. Cross-linking is determined to be complete once the last remaining frozen water has melted at the center of the forming hydrogel form, which can be easily observed because the forming hydrogel is substantially clear.

Very successful experiments have been performed according to this freeze-thaw technique to produce a solid hydrogel according to the invention in the shape of a human ear. Other structures that could be formed by this method, such as intervertebral discs, meniscus, etc. will be evident to those skilled in the art. It should be noted in this freeze-thaw technique, the threshold glass transition temperature of −80° C. for the mold material is selected to correspond roughly with the surface temperature of solid $CO_2$ (dry ice), to ensure the mold material does not become brittle when the first solution is frozen to produce the solid ice form. However, if another cooling material, other than $CO_2$ is used, then the threshold glass transition temperature for suitable mold materials may be adjusted accordingly.

For the three methods of hydrogel formation described above, the first solution contained both the peroxidase and T-HA, while the second solution contained the peroxide. While it may be possible to switch the peroxidase and peroxide in the first and second solutions respectively, it is less preferred to provide the peroxide in the first solution with the T-HA. This is because once the peroxide, peroxidase and T-HA are combined, the T-HA rapidly begins to form a cross-linked macromolecular network. If the peroxidase (which is a macromolecular molecule) is not already uniformly distributed with the T-HA it may be unable or substantially hindered from diffusing through the pore structure of the forming hydrogel to facilitate uniform cross-linking throughout the entire T-HA/peroxide solution. The result could be non-uniform and/or incomplete cross-linking of the T-HA and a non-uniform hydrogel. Conversely, the relatively small peroxide molecule (hydrogen peroxide is only one oxygen atom larger than water) can diffuse through the hydrogel pore structure with relative ease, resulting in a uniform hydrogel structure.

In addition, the macromolecular size of the peroxidase allows it to be similarly retained as the T-HA within porous molds that are only porous to small molecular weight peroxides which easily and uniformly diffuse through both the molds and newly forming macromolecular networks (i.e. hydrogels). For these reasons it is preferred to start with the peroxidase uniformly distributed with the T-HA in the first solution, and to provide the peroxide separately in the second solution.

A fourth method is an alternating sprayed or brushed layering technique. The first solution is prepared as described above and contains both the peroxidase and T-HA. However, the second solution not only contains the peroxide as described above, but also T-HA at the same concentration as in the first solution. Then a thin layer of the first solution is applied at the desired location (in situ) followed by an overlying thin layer of the second solution. This procedure is repeated such that alternating layers of the first and second solutions are successively applied until the defect or application situs has been completed. The very thin alternating layers of the first and second solutions promote virtually complete dityramine cross-linking ensuring a highly coherent final hydrogel having the desired Theological properties based on the initial T-HA concentration of the two solutions. The thin nature of the layers is desirable to ensure that free radicals produced by the peroxidase in the first solution layers are able to penetrate completely adjacent second solution layers and complete cross-linking independent of peroxidase diffusion into the second solution layer (see above). T-HA is included in both solutions to ensure uniform T-HA concentration throughout the final hydrogel. This technique has been performed in laboratory bench experiments and has provided contour-conforming and volumefilling coherent hydrogels. This technique is highly applicable where it is desired to provide a thin, but variable layer of tyramine cross-linked HA, such as on the surface of a denuded osteoarthritic joint in which little if any native healthy cartilage remains in the patient at the implant site.

All four of the above techniques have been described with respect to dityramine cross-linked hyaluronan, however it will be understood that other combinations within the scope of the present invention (other dihydroxyphenyl cross-linked macromolecules, such as polycarboxylates, polyamines, polyhydroxyphenyl molecules and copolymers thereof) can be molded via the above techniques.

Example 5

Figure 5:
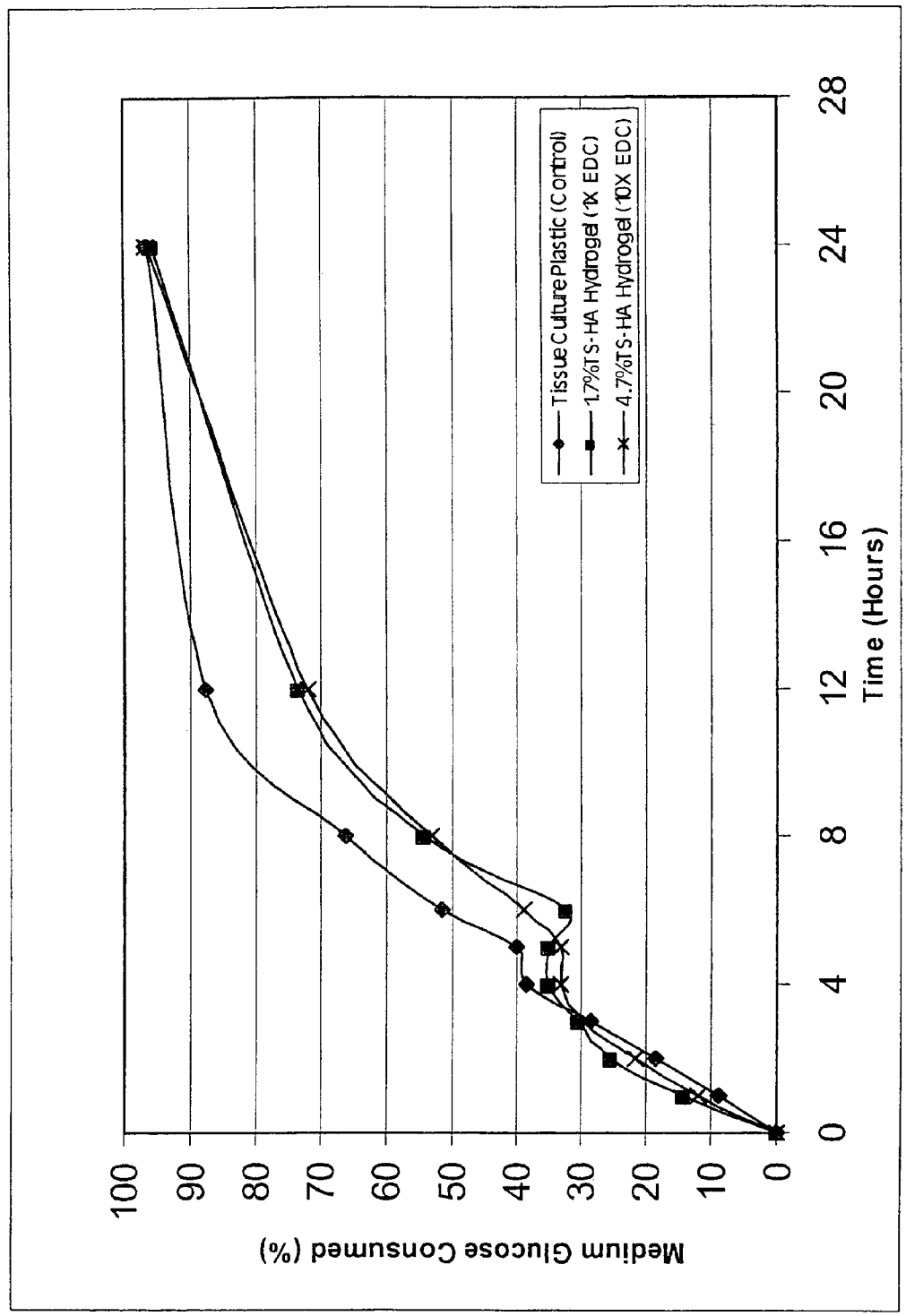
FIG. 5 is a graph showing comparative data of glucose utilization for chondrocytes embedded in T-HA hydrogels (1.7% and 4.7% T-HA) compared to cultured on tissue culture plastic (control).

Rat chondrocytes were embedded in (cross-linked) T-HA hydrogels to measure their ability to survive the cross-linking reaction. Isolated chondrocytes were suspended in the 1.7% and 4.7% T-HA hydrogels described in Example 2 by providing these live cells to the first solution to be co-dispersed with the T-HA and peroxidase, followed by introduction of the peroxide-containing second solution to initiate dityramine cross-linking. The chondrocyte-embedded 1.7% and 4.7% T-HA hydrogels exhibited uniformly distributed chondrocytes with the optical clarity of the gels allowing visualization throughout the gel. Glucose utilization was used as an indicator of cell viability after cross-linking to form the hydrogels as chondrocytes are voracious with respect to glucose consumption, depleting the medium of glucose in less than 24 hours. The results showed that chondrocytes embedded in T-HA hydrogels showed essentially the same glucose consumption profile over 24 hours as the same chondrocytes cultured in monolayer (FIG. 5). This continued for up to 7 days indicating that the cells were alive and metabolically active. Medium glucose was measured by standard hexokinase assay.

Fluorescent images of frozen sections of T-HA hydrogels containing both chondrocytes and cartilage tissue were also generated. HA samples from both the hydrogel scaffold and cartilage matrix were visualized by fluorescent staining with biotinylated HA binding protein (b-HABP) reagent while cell nuclei were visualized with standard DAPI stain. The b-HABP reagent is prepared from purified cartilage aggrecan (the G1 domain only) and link protein, and recognizes and irreversibly binds to stretches of native HA equivalent to those normally bound by aggrecan and link protein in cartilage. The results showed a more intense staining of the T-HA hydrogel with b-HABP than the cartilage as the hyaluronan in the tissue is already occupied by native aggrecan and link protein. No visible distinction could be seen between the T-HA scaffold of the hydrogel and the matrix of suspended cartilage tissue suggesting seamless integration. These results demonstrated the feasibility of maintaining the viability of chondrocytes during the hydrogel cross-linking reactions, and the ability of the hydrogel to integrate seamlessly into existing cartilage matrix, both of which are advantageous for application to cartilage repair. The results also demonstrated that sufficient stretches of the T-HA remain chemically unaltered, and available for binding by newly synthesized aggrecan and link protein in situ. The results also demonstrated that oxygen, carbon dioxide, glucose and insulin are diffusable through the T-HA hydrogels according to the invention at a rate that is not limiting to chondrocyte metabolism, which is important not only to the development of cartilage substitutes but to other applications such as glucose sensor design and development of an artificial kidney.

In order to include cells such as chondrocytes in hydrogels molded into intricate anatomical shapes using the freeze/thaw technique described in Example 4, it is desirable that the enzyme driven cross-linking reaction proceed in the presence of standard cell freezing solutions such as those containing 10% dimethylsulfoxide (DMSO)/90% fetal bovine serum (FBS). This has been demonstrated in the laboratory for all of the T-HA hydrogel formulations described in Example 3. The ability to directly incorporate a solution containing 90% FBS also demonstrates the ability to include bioactive factors such as growth factors, hormones and factors controlling cell differentiation, as these are normal components of FBS.

Although the above-described embodiments constitute the preferred embodiments, it will be understood that various changes or modifications can be made thereto without departing from the spirit and the scope of the present invention as set forth in the appended claims.

What is claimed is:

1. A method of making a macromolecular network comprising the steps of synthetically substituting hydroxyphenyl groups onto a first macromolecular species selected from the group consisting of polycarboxylates, polyamines, and copolymers thereof, and forming at least one dihydroxyphenyl linkage between two hydroxyphenyl groups that have been attached respectively to adjacent ones of said first macromolecular species.

2. A method according to claim 1, further comprising preparing said hydroxyphenyl-substituted polycarboxylates by carrying out a chemical reaction between a polycarboxylate and a second species comprising a primary amine group and a hydroxyphenyl functional group.

3. A method according to claim 1, further comprising preparing said hydroxyphenyl-substituted polyamines by carrying out a chemical reaction between a polyamine and a second species comprising a $CO_2H$ group and a hydroxyphenyl functional group.

4. A method according to claim 2, said second species being tyramine or tyrosine.

5. A method according to claim 3, said second species being tyrosine, 4-hydroxyphenylacetic acid, or 3-(4-hydroxyphenyl)propionic acid.

6. A method according to claim 2, said polycarboxylate being hyaluronan.

7. A method according to claim 2, said polycarboxylate being chondroitin sulfate.

8. A method according to claim 2, said second species being tyramine and said polycarboxylate being hyaluronan, the resulting macromolecular network being a dityramine cross-linked network of tyramine-substituted hyaluronan molecules.

9. A method according to claim 2, said chemical reaction being carried out in a pH range of 6-7.

10. A method according to claim 2, said chemical reaction being carried out via the following pathway:
   a) reacting a carboxylic acid group on said polycarboxylate with a carbodiimide to form an O-acylisourea-substituted polycarboxylate, and
   b) reacting said O-acylisourea-substituted polycarboxylate with the primary amine group on said second species to form said hydroxyphenyl-substituted polycarboxylate.

11. A method according to claim 3, said chemical reaction being carried out via the following pathway:
   a) reacting said $CO_2H$ group on said second species with a carbodiimide to form an O-acylisourea-substituted second species, and b) reacting said O-acylisourea-substituted second species with a primary amine group on said polyamine to form said hydroxyphenyl-substituted polyamine.

12. A method according to claim 10, said carbodiimide being 1-ethyl-3-(3-dimethylaminopropyl)carbodiimide.

13. A method according to claim 10, step (a) being carried out in the presence of an active ester forming catalyst.

14. A method according to claim 13, said catalyst being N-hydroxysuccinimide.

15. A method according to claim 1, further comprising forming said dihydroxyphenyl linkage by reacting said hydroxyphenyl groups with a peroxide in the presence of an enzyme to yield adjacent hydroxyphenyl free radical species, said free radical species dimerizing via a dimerization reaction to yield said dihydroxyphenyl linkage.

16. A method according to claim 15, said peroxide being hydrogen peroxide and said enzyme being horseradish peroxidase.

17. A method of making a hydrogel comprising the steps of:
   a) providing a first solution comprising either a peroxidase enzyme or a peroxide but not both, and also a macromolecular species selected from the group consisting of hydroxyphenyl-substituted polycarboxylates, hydroxyphenyl-substituted polyamines, other polyhydroxyphenyl molecules, and copolymers thereof;
   b) providing a second solution comprising the one of said peroxidase enzyme or peroxide not provided in said first solution; and
   c) combining said first and second solutions to initiate dihydroxyphenyl cross-linking to form said hydrogel.

18. A method according to claim 17, further comprising providing a non-porous mold having an inner mold cavity conforming to the shape, contour and volume of a desired hydrogel part, and combining said first and second solutions within said inner mold cavity to form said hydrogel in the shape thereof.

19. A method according to claim 17, further comprising the steps of:
   d) providing a mold made from porous material having an inner mold cavity conforming to the shape, contour and volume of a desired hydrogel part;
   e) providing said first solution into said inner mold cavity of said mold; and
   f) immersing said porous mold having said first solution therein in a bath of said second solution to thereby initiate said dihydroxyphenyl cross-linking and formation of said hydrogel.

20. A method according to claim 17 further comprising the steps of:
   d) providing a mold made from a pliable material having an inner mold cavity conforming to the shape, contour and volume of a desired hydrogel part;
   e) providing said first solution into said inner mold cavity of said mold;
   f) cooling said mold to freeze said first solution within the inner mold cavity thereof to provide a solid ice form in the shape of said inner mold cavity; and
   g) immersing said solid ice form in a bath of said second solution to thereby initiate thawing of frozen water and dihydroxyphenyl cross-linking to form said hydrogel.

21. A method according to claim 20, said pliable material being a polymeric material having a glass-transition temperature less than about −80° C.

22. A method according to claim 20, said cooling step being carried out by contacting said mold and its contents with dry ice.

23. A method according to claim 20, further comprising demolding said solid ice form from said mold prior to immersion of said solid ice form.

24. A method a according to claim 20, said pliable material having a glass transition temperature lower than the temperature at which said first solution is frozen in said cooling step.

25. A method according to claim 17, said second solution further comprising said macromolecular species, the method further comprising alternately applying layers of the first and second solutions to a situs to thereby initiate said dihydroxyphenyl cross-linking and formation of said hydrogel.

26. A method according to claim 17, said first solution comprising a peroxidase.

27. A method according to claim 17, said macromolecule being tyramine-substituted hyaluronan.

* * * * *